(12) United States Patent
Veatch

(10) Patent No.: US 10,292,839 B2
(45) Date of Patent: May 21, 2019

(54) GRIPPING DEVICE WITH SWITCHABLE PREHENSION MODES

(71) Applicant: Invisible Hand Enterprises, LLC, Westminster, CO (US)

(72) Inventor: Bradley Delton Veatch, Westminster, CO (US)

(73) Assignee: Invisible Hand Enterprises, LLC, Westminster, CO (US)

(*) Notice: Subject to any disclaimer, the term of this patent is extended or adjusted under 35 U.S.C. 154(b) by 0 days.

(21) Appl. No.: 15/412,905

(22) Filed: Jan. 23, 2017

(65) Prior Publication Data

US 2017/0209288 A1    Jul. 27, 2017

Related U.S. Application Data

(60) Provisional application No. 62/281,647, filed on Jan. 21, 2016.

(51) Int. Cl.
| | |
|---|---|
| *A61F 2/58* | (2006.01) |
| *A61F 2/50* | (2006.01) |
| *A61F 2/74* | (2006.01) |

(52) U.S. Cl.
CPC ...... *A61F 2/588* (2013.01); *A61F 2002/5007* (2013.01); *A61F 2002/741* (2013.01); *A61F 2002/745* (2013.01); *A61F 2002/747* (2013.01)

(58) Field of Classification Search
CPC .. A61F 2/58; A61F 2/583; A61F 2/586; A61F 2/588
See application file for complete search history.

(56) References Cited

U.S. PATENT DOCUMENTS

| | | | |
|---|---|---|---|
| 1,423,296 A | 7/1922 | Francis | |
| 1,608,689 A | 11/1926 | Frederick | |
| 1,742,269 A | 1/1930 | McElroy | |
| 2,285,885 A | 6/1942 | Becker | |

(Continued)

*Primary Examiner* — Bruce E Snow
(74) *Attorney, Agent, or Firm* — IP Alternative, LLC

(57) ABSTRACT

The present disclosure relates to a switchable terminal device that includes a first digit having a distal end and a proximal end, a second digit moveably attached to the first digit by a first connector such that the second digit reversibly rotates around the first connector and substantially within a plane, and a lever guide having a first portion and a second portion, the lever guide attached to the second digit at least by the first connector passing through the lever guide at an angle about perpendicular to the plane. The switchable terminal device also includes a lever having a proximal end and a distal end with the proximal end of the lever moveably attached to the first portion of the lever guide by a second connector, a third connector attached near the distal end of the first digit, and an elastic cord that includes a first segment having a first end, and a second segment having a second end. Further, the first end is attached to the first portion of the lever guide, a first part of the first segment contacts the second portion of the lever guide, a second part of the first segment spans a first distance between the lever guide and the third connector, a first part of the second segment spans a second distance between the third connector and the distal end of the lever, and the second end of the elastic cord is attached to the lever.

19 Claims, 17 Drawing Sheets

(56) References Cited

U.S. PATENT DOCUMENTS

| | | |
|---|---|---|
| 2,364,313 A | 12/1944 | Pecorella |
| 2,549,074 A | 4/1951 | Meyer et al. |
| 4,685,924 A | 8/1987 | Massey |
| 4,685,929 A | 8/1987 | Monestier |
| 6,010,536 A * | 1/2000 | Veatch .................... A61F 2/588 414/6 |
| 7,341,295 B1 | 3/2008 | Veatch et al. |
| 2014/0081425 A1 | 3/2014 | Sensinger |

* cited by examiner

GRIPPING DEVICE WITH SWITCHABLE PREHENSION MODES

CROSS-REFERENCE TO RELATED APPLICATIONS

This application claims the benefit of U.S. Provisional Patent Application No. 62/281,647, filed on Jan. 21, 2016, entitled "Gripping Device with Switchable Prehension Modes", which is incorporated herein by reference in its entirety.

BACKGROUND

The following text should not be construed as an admission of knowledge in the prior art. Furthermore, citation or identification of any document in this application is not an admission that such document is available as prior art to the present invention, or that any reference forms a part of the common knowledge in the art.

In the field of prosthetics, many components are operated using power harvested from the user's own musculature using harnessing and a Bowden cable like those used for bicycle brakes and derailleurs. This form of operation is called body-powered, or BP. One such BP component is called a terminal device (TD) or gripper, and its function is to replace a missing hand for upper-limb amputees. It is a device that permits the user to grasp objects. Two configurations of TD are commonly used: voluntary-opening (VO), and voluntary-closing (VC).

With VO operation, the terminal device opens as the user increases their cable tension, due to an applied force. To grasp an object, they first apply a force to open the TD to larger than they require for the object, called sizing, or sizing the aperture, and then they move the TD around the object or bring the object between the grasping digits, hook structures, etc. Relaxing the cable tension allows the device to close and apply a prehension force to the object. This system behaves mechanically identical to a spring-loaded clamp.

Advantages of VO devices are that the TD will grasp an object even if the user allows the cable tension to vanish or go slack. This prevents muscle fatigue. The devices are very simple, and use replaceable rubber bands or springs to generate a prehension force. Drawbacks are that the prehension or pinch force maximum is set by the strength of the rubber bands. Many users add bands to generate a higher force, but then must modulate the cable tension to avoid crushing delicate objects. This requires muscular exertion to offset a portion of the pinch force, causing fatigue and over a period time secondary health consequences that can be debilitating and even devastating. Repetitive stress or overuse syndrome, cumulative traumatic injury, pain, loss of bodily function, and significant medical treatment costs are common, along with lost work.

However, if the user operates the cable such that it is rarely allowed to go slack, the user can develop a sense for how much pinch force they are applying. This ability to sense objects through the cable is called physiological proprioception. It is the same physiological connection that allows a tennis racket, golf club, bat, etc. to become an extension of the user's body; they know precisely where in space around their body the instrument is and are able to use it with extraordinary skill. Cable-operated, or BP terminal devices also preserve proprioception and this is one of the primary reasons they remain popular over more sophisticated technologies.

Voluntary-closing devices actuate in exactly the opposite manner. As the user increases their cable tension, the device closes to apply a prehension force. Advantages are the device preserves proprioception, and pinch force is proportional to the cable tension, due to the applied force, allowing the user to "feel" the object being grasped, and operation is more intuitive to the user. Maximum pinch force is determined by the user's strength, not elastic bands as with VO operation. Drawbacks of VC operation are that at rest, the TD is open, which can be awkward when it is not being used. Also, to sustain prehension, the user must sustain their cable tension, often resulting in fatigue or dropping objects if the user moves their torso and cable tension fluctuates. For general carrying or holding objects passively, VO operation is preferred, while dexterous tasks benefit from VC operation. Each mode has its applications and areas of performance where it excels.

At least two reasons exist that have inhibited the development of a gripping device with a simple design for easily switching between prehension modes. First, in VO mode, the TD is held closed with a strong spring force. In VC mode, it must be held open with a weak or light force to avoid fatiguing the user. Changing positions of the moving digit from open to close while simultaneously changing the spring force is a difficult engineering problem. Second, the device must change operating modes from VO to VC and back without changing the cable resting position. If the cable moves or suddenly gets tensioned or highly slack, the user will be unable to operate the device without having to adjust their harness. This is difficult for an amputee to achieve. Harness and cable settings are exquisitely sensitive to variation and minor changes can render the system unusable. This is one of the chief reasons upper limb prosthetic fitting and adjustment is considered very difficult and an area of prosthetic expertise.

Thus, it is clearly evident that there is a long-felt need in the field of prosthetics for a body-actuated gripping device with an easily switchable prehension mode (from VO mode to VC mode and back again), that is also simple in design and operation, easy to manufacture, and economical from both a purchase price perspective and maintenance perspective.

SUMMARY

An aspect of the present disclosure is a switchable terminal device that includes a first digit having a distal end and a proximal end, a second digit moveably attached to the first digit by a first connector such that the second digit reversibly rotates around the first connector and substantially within a plane, and a lever guide having a first portion and a second portion, the lever guide attached to the second digit at least by the first connector passing through the lever guide at an angle about perpendicular to the plane. The switchable terminal device also includes a lever having a proximal end and a distal end with the proximal end of the lever moveably attached to the first portion of the lever guide by a second connector, a third connector attached near the distal end of the first digit, and an elastic cord that includes a first segment having a first end, and a second segment having a second end. Further, the first end is attached to the first portion of the lever guide, a first part of the first segment contacts the second portion of the lever guide, a second part of the first segment spans a first distance between the lever guide and the third connector, a first part of the second segment spans a second distance between the third connector and the distal end of the lever, and the second end of the elastic cord is attached to the lever.

In some embodiments of the present disclosure, the second portion of the lever guide may be substantially cylindrical, the second portion of the lever guide may include an outer edge, the first connector may be positioned substantially centrally located in the second portion of the lever guide relative to the plane, and the first part of the first segment may contact at least a portion of the edge. In some embodiments of the present disclosure, the outer edge may include a groove, and the first part of the first segment may be positioned within the groove. In some embodiments of the present disclosure, the third connector may include a rod extending from the first digit substantially perpendicular to the plane. In some embodiments of the present disclosure, the third connector may further include a pulley rotatably attached to the rod, and the elastic cord may be in contact with the pulley.

In some embodiments of the present disclosure, the first portion of the lever guide may include a first channel, and the proximal end of the lever may be positioned within the first channel. In some embodiments of the present disclosure, the first portion of the lever guide may include a second channel, and a fraction of the first segment may be positioned within the second channel. In some embodiments of the present disclosure, the distal end of the lever may include a third channel positioned within and along at least a portion of the lever, and a fraction of the second segment may be positioned within the third channel.

In some embodiments of the present disclosure, the lever may have a first position corresponding to the distal end of the lever positioned towards a palmar side of the fixed digit, the lever may have a second position corresponding to the distal end of the lever positioned towards a dorsal side of the fixed digit, and the lever is reversibly switched between the first position and the second position. In some embodiments of the present disclosure, when in the first position, the distal end of the lever is positioned towards the distal end of the fixed digit or towards the proximal end of the fixed digit, when in the second position, the distal end of the lever is positioned towards the distal end of the fixed digit or towards the proximal end of the fixed digit, when the distal end of the lever is in the first position and positioned towards the distal end of the fixed digit, the tension cord provides a first force, and when the distal end of the lever is in the second position and positioned towards the distal end of the fixed digit, the tension cord provides a second force that is greater than the first force. In some embodiments of the present disclosure, the first force may be between about 2 $lb_f$ and about 5 $lb_f$. In some embodiments of the present disclosure, when the distal end of the lever is in the second position, the first segment and the second segment may form at least one of a crossing point or a contact point, and when the distal end of the lever is in the first position, the first segment and the second segment may not form the crossing point or the contact point.

In some embodiments of the present disclosure, the first connector may include at least one of a pin, a screw, a rivet, a nail, a shaft, and/or a rod. In some embodiments of the present disclosure, the switchable terminal device may further include a locking mechanism positioned at the third connector, wherein the locking mechanism has a locked position and an unlocked position, the locked position prevents the second digit from rotating around the first connector, and the unlocked position allows the second digit to rotate around the first connector.

An aspect of the present disclosure is a method for actuating a switchable terminal device, where the method includes attaching, using a connector, a first digit having a distal end and a proximal end to a second digit, where the second digit is rotatable relative to the first digit, around the first connector, and substantially within a first plane; affixing a lever guide having a first portion and a second portion to the second digit such that the first connector passes through a point substantially near the center of the lever guide at an angle about perpendicular to the first plane; securing a lever having a proximal end and a distal end by moveably attaching the proximal end of the lever to the first portion of the lever guide using a second connector; positioning a third connector near the distal end of the first digit; attaching to the lever guide an elastic cord that includes a first segment having a first end, and a second segment having a second end, such that the first end is attached to the first portion of the lever guide; passing at least a part of the first segment over the second portion of the lever guide; traversing with the first segment a first distance between the lever guide and the third connector; contacting the third connector with a portion of the elastic cord; traversing with the second segment a second distance between the lever guide and the distal end of the lever; and connecting the second end to the distal end of the lever.

In some embodiments of the present disclosure, the method may further include reversibly switching the lever from a first position corresponding to the distal end of the lever positioned towards a palmar side of the fixed digit to a second position corresponding to the distal end of the lever positioned towards a dorsal side of the fixed digit, where the switching may be performed by moving the distal end of the lever through a second plane that is not parallel to the first plane. In some embodiments of the present disclosure, when in the first position, actuating the distal end of the lever by moving the distal end of the lever from a first distal location to a first proximal location may result in the terminal device transitioning from open to closed, and when in the second position, actuating the distal end of the lever by moving the distal end of the lever from a second distal location to a second proximal location may result in the terminal device transitioning from closed to open.

In some embodiments of the present disclosure, the method may further include, when in the first position and the first distal location, applying a first force to the distal end of the lever, that is less than a second force applied to the distal end of the lever when in the second position and the second distal location. In some embodiments of the present disclosure, the method may further include crossing the first segment relative to the second segment when switching the lever from the first position to the second position, and uncrossing the first segment relative to the second segment when switching the lever from the second position to the first position.

An aspect of the present disclosure is a locking mechanism that includes a drum (cylindrical lever guide) separated from a plate by a space having a narrow section and a wide section, and a disk moveable between a first position and a second position along a first path within a first plane, where when the disk is in the first position, the disk is positioned on the first path in the narrow section such that the disk is in physical contact with the drum and the plate such that the drum may not rotate, and when the disk is in the second position, the disk is positioned on the first path in the wide section such that the disk does not contact the drum or the plate such that the drum is free to rotate.

BRIEF DESCRIPTION OF THE DRAWINGS

Some embodiments of the present disclosure are illustrated in referenced figures of the drawings. It is intended that the embodiments and figures disclosed herein are to be considered illustrative rather than limiting.

Figure 1:
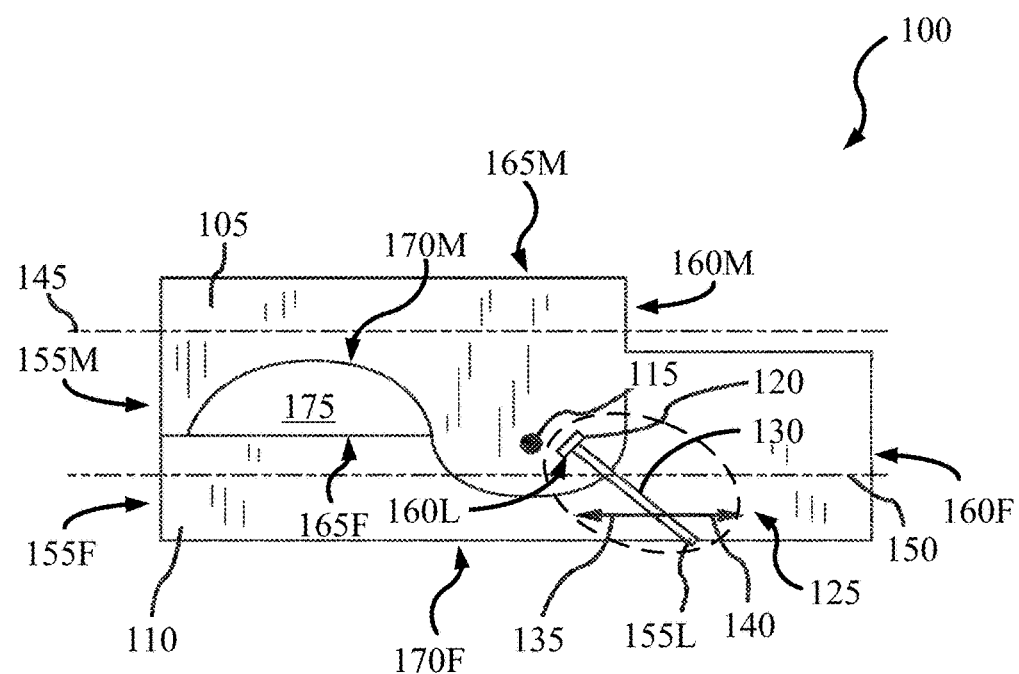
FIG. 1 illustrates a switchable prehensor in voluntary closed mode, in the closed position, according to some embodiments of the present disclosure.

| REFERENCE NUMBERS | |
|---|---|
| 100 | terminal device |
| 105 | moveable digit |
| 110 | fixed digit |
| 115 | first connector |
| 120 | second connector |
| 125 | switchable biasing mechanism |
| 130 | lever |
| 135 | first force-generating mechanism |
| 140 | second force-generating mechanism |
| 145 | first axis |
| 150 | second axis |
| 155 | distal end |
| 160 | proximal end |
| 165 | dorsal side |
| 170 | palmar side |
| 175 | gap |
| 500 | lever guide |
| 510 | first channel |
| 520 | securement point |
| 530 | cable guide |
| 540 | first stop |
| 550 | second stop |
| 560 | anchor point |
| 570 | flag |
| 580 | VC passive length |
| 590 | VO passive length |
| 900 | first segment |
| 910 | second segment |
| 920 | first end |
| 930 | second end |
| 940 | second channel |
| 950 | third channel |
| 960 | third connector |
| 970 | drum |
| 980 | pulley |
| 990 | stopper |
| 1000 | locking mechanism |
| 1010 | disk |
| 1020 | magnet |
| 1030 | plate |
| 1040 | handle |

DETAILED DESCRIPTION

The following detailed description illustrates the invention by way of example and not by way of limitation. References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. The term "substantially" and "about" refer to the inherent error in any numerical measurement and that any number and/or range of numbers cannot not be measured and reported exactly. Thus, the terms "substantially" and "about" refer to +/−error limits to such numerical elements. In some embodiments, "substantially" and "about" may refer to error limits from +/−0.1% to about +/−10%.

The present disclosure relates to a terminal device that achieves two beginning states, one the "at rest" (or passive state) VO position with the digits of the terminal device closed, and the second the "at rest" (or passive state) VC position with the digits of the terminal device open, using an over-the-center switchable biasing mechanism that changes the direction of the torque and/or moment about the moveable digit's pivot as well as its magnitude. An innovative aspect of this switchable biasing mechanism is the use of a spatial mechanism; an over-the-center lever moves out of the plane in which the remaining mechanism operates. The present disclosure also relates to a terminal device design that exploits geometric symmetry about the over-the-center switchable biasing mechanism that allows the initial starting cable excursion positions to be identical, thereby eliminating problems that arise when initial cable positions change. The present disclosure also describes the relationships between the switchable biasing mechanism and force-generating mechanisms used to passively open and/or close the terminal device, when in VC mode and/or VO mode, respectively. Thus, in some embodiments of the present disclosure, a first force-generating mechanism, an elastic tension cord, whose geometry relative to the positioning of the over-the-center lever provides control of the passive forces provided to the terminal device. For example, the relative positioning and/or dimensions of the lever, the lever's point of rotation, the tension cord, the tension cord's attachment location to the lever, and/or the tension cord's attachment location to the fixed digit of the terminal device enable the passive force provided by the tension cord when in VO mode to be higher than the passive force provided by the tension cord when in VC mode.

As used herein, the term "terminal device" refers to a gripping device and/or a prosthetic device, wherein such a device includes one or more digits suitable for grasping, gripping, grabbing, holding, or performing other actions commonly performed by one or more fingers or a hand. As used herein, the term "digit" is synonymous with lever, phalange, and/or phalanx, or a joined collection of phalangeal segments constituting a grasping member or finger. A digit may have a relatively flat, planar structure, with just sufficient thickness to provide structural and mechanical support. Alternatively, a digit may include three dimensions that are roughly proportional to a natural human finger.

As described herein, some embodiments of a terminal device have a moveable digit, where the moveable digit has a dorsal side, a palmar side, a distal end, and a proximal end, such that the distal end and the proximal end are aligned along a first axis. Thus, the moveable digit may be divided into a distal portion and a proximal portion. The terminal device also includes a fixed digit, where the fixed digit has a dorsal side, a palmar side, a distal end, and a proximal end, such that the distal end of the fixed digit and the proximal end of the fixed digit are aligned along a second axis. Thus, the fixed digit may also be divided into a distal portion and a proximal portion. In some embodiments of the present disclosure, the distal portion and proximal portion of the fixed digit may be approximately equal in length relative to the second axis. The distal portion of the moveable digit may be substantially aligned with the distal portion of the fixed digit when the terminal device is in the closed position and/or substantially in the closed position. Similarly, when the terminal device is in the closed position, the first axis and the second axis may be parallel and/or substantially parallel to each other. In general, "distal" refers to a location of an element along an axis positioned away from a reference point; e.g. the user, a connector, etc. In general, "proximal" refers to a location of an element along an axis positioned close to the reference point. In general, "dorsal" refers to a location of an element that is positioned above a reference point. In general, "palmar" refers to a location of an element that is positioned below a reference point.

The moveable digit and the fixed digit are moveably connected to each other such that the moveable digit may rotate around a third axis that is substantially perpendicular to both the first axis and the second axis. Thus, the terminal device may have a first connector that attaches the moveable digit to the fixed digit, with some examples of a first connector including a cylindrical structure, such as a pin, a nail, a screw, a rod, a rivet, a rod, a post, and/or a circular section of cord tied into a loop. In some embodiments of the present disclosure, the first connector may be positioned on the terminal device such that the first connector marks the transition that divides the fixed digit into its proximal portion and its distal portion. Further, the first connector may be positioned substantially on the palmar side of the moveable digit and substantially on the dorsal side and/or towards the midline of the fixed digit. In some embodiments of the present disclosure, the first connector may have a dorsal side, a palmar side, a distal side, and/or a proximal side, where all of these sides are relative to the dorsal side, palmar side, distal end, and proximal end of the fixed digit. In some embodiments of the present disclosure, the first connector may be attached and/or connected to the fixed digit at or near the middle of the fixed digit (e.g. at or near the transition from the distal portion to the proximal portion of the fixed digit). In some embodiments of the present disclosure, the first connector may be attached to the proximal portion of the moveable digit such that the moveable digit may rotate around the first connector, enabling the terminal device to reversibly switch and move between an "open position" and a "closed position" when in either VC mode or VO mode. Thus, the moveable digit may rotate relative to the fixed digit around a pivot point created by the first connector, such that when the terminal device is in the closed position, the first and second axis are substantially parallel, and the palmar side of the moveable digit faces the dorsal side of the fixed digit. The terminal device also includes a switchable biasing mechanism, which may include a lever having a proximal end and a distal end, such that the first end of the lever is moveably attached to the moveable digit. Thus, the lever may be reversibly switched from a first position to a second position, where the first position includes positioning the distal end of the lever on the palmar side of the first connector and/or more towards the palmar side of the fixed digit (e.g. corresponding to the VC mode of operating the terminal device; see FIGS. 1 and 2), and the second position includes positioning the distal end of the lever on the dorsal side of the first connector and/or more towards the dorsal side of the moveable digit (e.g. corresponding to the VO mode of operating the terminal device; see FIGS. 3 and 4).

FIG. 1 illustrates an example of a terminal device 100 according to some embodiments of the present disclosure, where the terminal device 100 includes a moveable digit 105, moveably connected to a fixed digit 110 by a first connector 115. The moveable digit 105 and/or the fixed digit 110 may be a simple digit, or it may be a complicated anthropomorphic representation of a human finger. The moveable digit 105 and/or the fixed digit 110 may include one or more joints. The moveable digit 105 and/or the fixed digit 110 may include an outer layer that imitates the look, texture and/or feel of skin. The moveable digit 105 and/or the fixed digit 110 may include a shape that facilitates gripping, grabbing, holding, and/or grasping an article. Referring to FIG. 1, in some embodiments of the present disclosure, the moveable digit 105 may have a palmar side 170M that has been fabricated to take the shape of an arc to form a gap 175 positioned between the palmar side 170M of the moveable digit 105 and a dorsal side 165F of the fixed digit 110, even when the terminal device 100 is in a closed position. Alternatively, there may be no gap 175 between the moveable digit 105 and the fixed digit 110 when the terminal device 100 is in the closed position. Alternatively, there may be some other geometrically shaped gap 175 created in the moveable digit 105, other than an arc, that forms a gap between the fixed digit 110 and the moveable digit 105, even when the terminal device 100 is in the closed position.

Referring again to FIG. 1, in some embodiments of the present disclosure, the fixed digit 110 may have a dorsal side 165F that has been fabricated to take the shape of an arc (not shown) to form a gap (not shown) between the palmar side 170M of the moveable digit 105 and the dorsal side 165F of the fixed digit 110, even when the terminal device 100 is in a closed position. Alternatively, there may be some other geometrically shaped gap (not shown) created in the fixed digit 110, other than an arc, that forms a gap between the fixed digit 110 and the moveable digit 105, even when the terminal device 100 is in the closed position.

In some embodiments of the present disclosure, the distal end 155F of the fixed digit 110 and the distal end 155M of the moveable digit 105 may have shapes adapted to help facilitate easier gripping, grasping, and/or grabbing of an object such as a pencil, a glass, a tool or some other specific device for a specific task. For example, the moveable digit 105, the fixed digit 110, or both may be provided with a groove and/or notch configured to receive a writing utensil. Referring again to FIG. 1, the first connector 115 may mechanically attach the moveable digit 105 to the fixed digit 110, such that the moveable digit 105 may rotate relative to the first connector 115. This rotation may be visualized by an axis (not shown) extending out of FIG. 1, perpendicular to the page from the first connector 115, such that the moveable digit 105 may rotate around this perpendicular axis.

Figure 2:
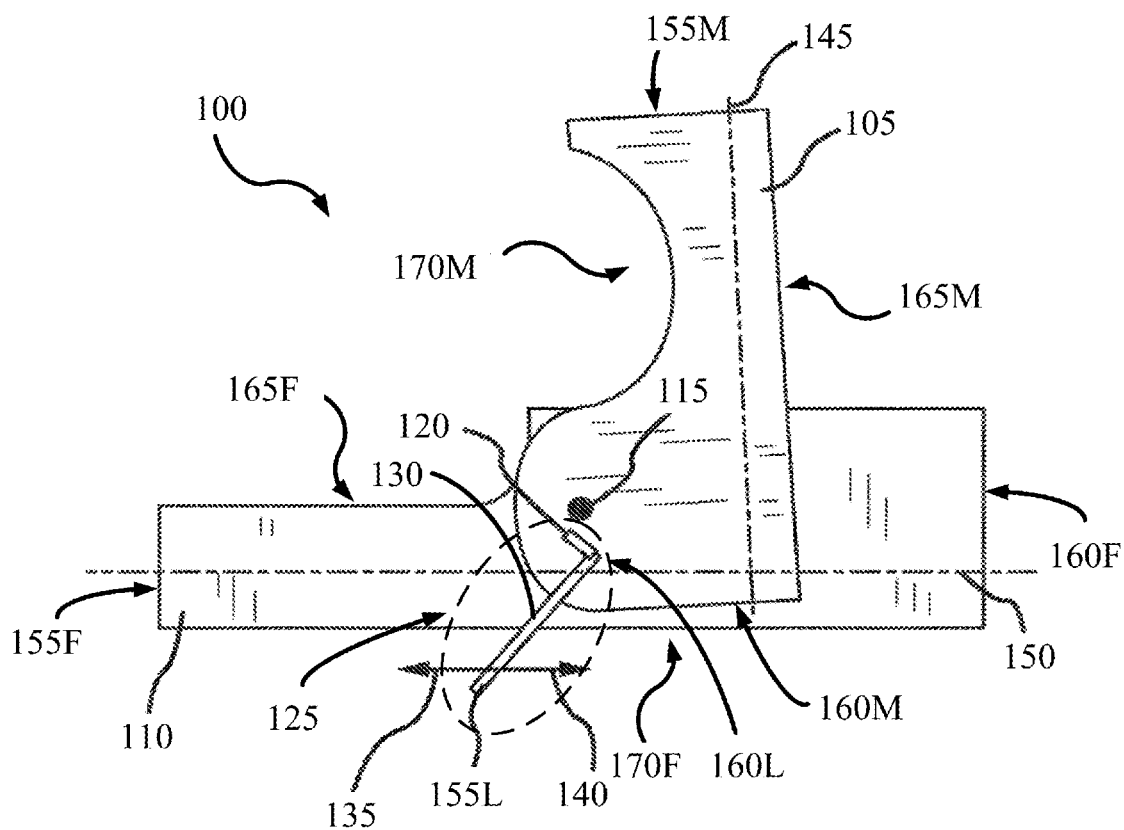
FIG. 2 illustrates a switchable prehensor in voluntary closed mode, in the open position, according to some embodiments of the present disclosure.

The terminal device 100 illustrated in FIG. 1 shows the terminal device 100 in a closed position. Referring to FIG. 2, the terminal device 100 is shown with its moveable digit 105 in an open position, rotated about 90 degrees (angle of rotation) around the first connector 115 relative to the closed position shown in FIG. 1. The moveable digit 105 and the fixed digit 110 may have aspect ratios similar to that of normal human fingers. The exact aspect ratios chosen for a particular application depends at least upon the overall size of the terminal device 100, which may vary depending on whom it is fitted for; e.g. children, versus small adults, versus large adults. In other applications, the moveable digit 105 and the fixed digit 110 may describe an aspect ratio significantly different from that normal for human fingers.

Referring again to FIGS. 1 and 2, both the moveable digit 105 and the fixed digit 110 may describe a length along a first axis 145 for the moveable digit 105 and along a second axis 150 for the fixed axis, respectively. In some embodiments of the present disclosure, the first axis 145 and the second axis 150 may be substantially parallel to each other when the terminal device 100 is in the closed position. When in the open position, the first axis 145 and the second axis 150 may be substantially perpendicular to each other and/or substantially non-parallel to each other. The movement of the moveable digit 105 may describe an arc created by the sweep of the distal end 155M of the moveable digit 105 around its point of rotation, the first connector 115, and/or relative to the fixed digit 110. This arc is referred to herein as the "angle of rotation". The angle of rotation may be between about 10° and about 180°, between about 30° and about 160°, between about 50° and about 140°, and/or between about 60° and about 120°.

In some embodiments of the present disclosure, the first connector 115 may be a substantially cylindrical feature positioned on either the moveable digit 105 and/or the fixed digit 110 such that the first connector 115 moves rotatably within a ring and/or annular structure on the opposing digit. The first connector 115 may also be a rounded "peninsular" tab located on either the moveable digit 110 and/or the fixed digit 110 such that the rounded "peninsular" tab rotates through a limited but adequate angle within the opposing digit, where the "adequate angle" may be substantially similar to the angle of rotation described above.

Referring again to FIGS. 1 and 2, the terminal device 100 includes a switchable biasing mechanism 125, which when manipulated by the user, reversibly switches the terminal device 100 between the VO mode of operation and the VC mode of operation. In some embodiments of the present disclosure, the switchable biasing mechanism 125 may include a lever 130 that is physically attached to a portion (e.g. the proximal portion and/or at the transition from the proximal portion to the distal portion) of the moveable digit 105 such that actuation (application and/or release of a force) of the lever 130 results in movement of the lever 130 in space (e.g. within the plane occupied by the fixed digit 110), resulting in movement of the moveable digit 100 relative to the fixed digit 110 and around the first connector 115 (e.g. a pin, screw, rivet, and/or a nail). Thus, as described in more detail below, a switchable biasing mechanism 125 may be used to reversibly switch the terminal device 100 between the VO mode of operation and the VC mode of operation and to actuate the terminal device 100 when configured for either mode.

When in the VC mode, as long as the active force is less than the passive force, the moveable digit 105 is positioned in the open position (FIG. 2) by the passive force that is continually provided by a first force-generating mechanism 135, e.g. a tension cord, elastic, and/or spring. However, when the user applies an active force that exceeds the passive force, utilizing a second force-generating mechanism 140, for example a body-actuated cable, the moveable digit 105 is moved to the closed position as shown in FIG. 1. When the user releases the second force-generating mechanism 140 (e.g. cable) such that the passive force again exceeds the active force, the moveable digit 105 returns from the closed position to the open position. As described above, and as shown in the examples illustrated in FIGS. 1-8, a switchable biasing mechanism 125 may include a lever 130 attached by a second connector 120 to the moveable digit 105. The first force-generating mechanism 135 and the second force-generating mechanism 140 may both be attached and applied to a distal end 155L of the lever 130, but in substantially opposing directions relative to the second axis 150. Thus, the second force-generating mechanism 140 may apply the active force such that the distal end 155L of the lever 130 is moved towards the proximal end 160F of the fixed digit 110 and, since the lever 130 is attached to the moveable digit 100 at the second connector 120, the movement of the lever 130 causes movement of the moveable digit 105 to the closed position. Similarly, movement of the moveable digit 105 back to the open position may be achieved when the user releases the second force-generating mechanism 140, for example by releasing the cable, such that the passive force generated by the first force-generating mechanism 135 exceeds the active force generated by the second force-generating mechanism 140, resulting in the first force-generating mechanism 135 moving the distal end 155L of the lever 130 towards the distal end 155F of the fixed digit 110, causing the return of the moveable digit 105 to the open position as shown in FIG. 2.

As shown in FIGS. 1-4, in some embodiments of the present disclosure, the switchable biasing mechanism 125 includes a lever 130, such that the proximal end 160L of the lever 130 is moveably attached to the second connector 120, and the second connector 120 is positioned near the first connector 115. For example, the proximal end 160L of the lever 130 may be positioned distally to the first connector 115, proximally to the first connector 115, or substantially adjacent to the first connector 115 on either its dorsal side or palmar side.

Figure 3:
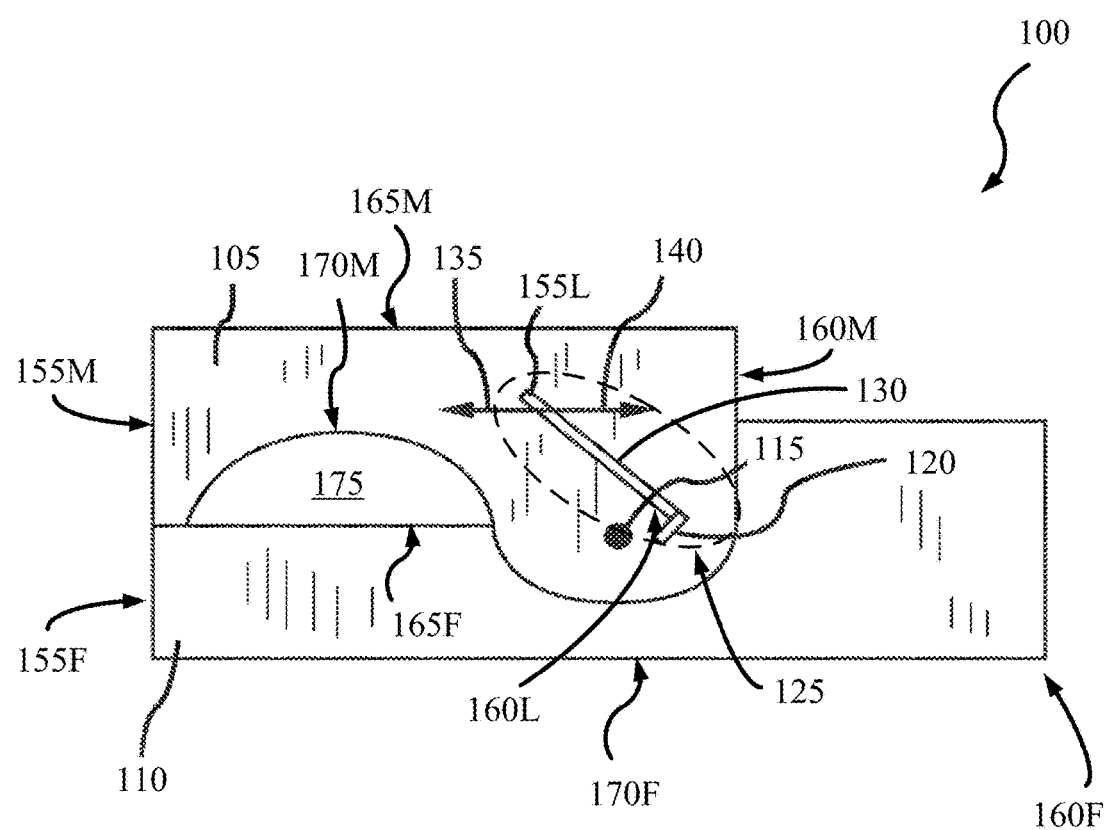
FIG. 3 illustrates a switchable prehensor in voluntary open mode, in the closed position, according to some embodiments of the present disclosure.
Figure 4:
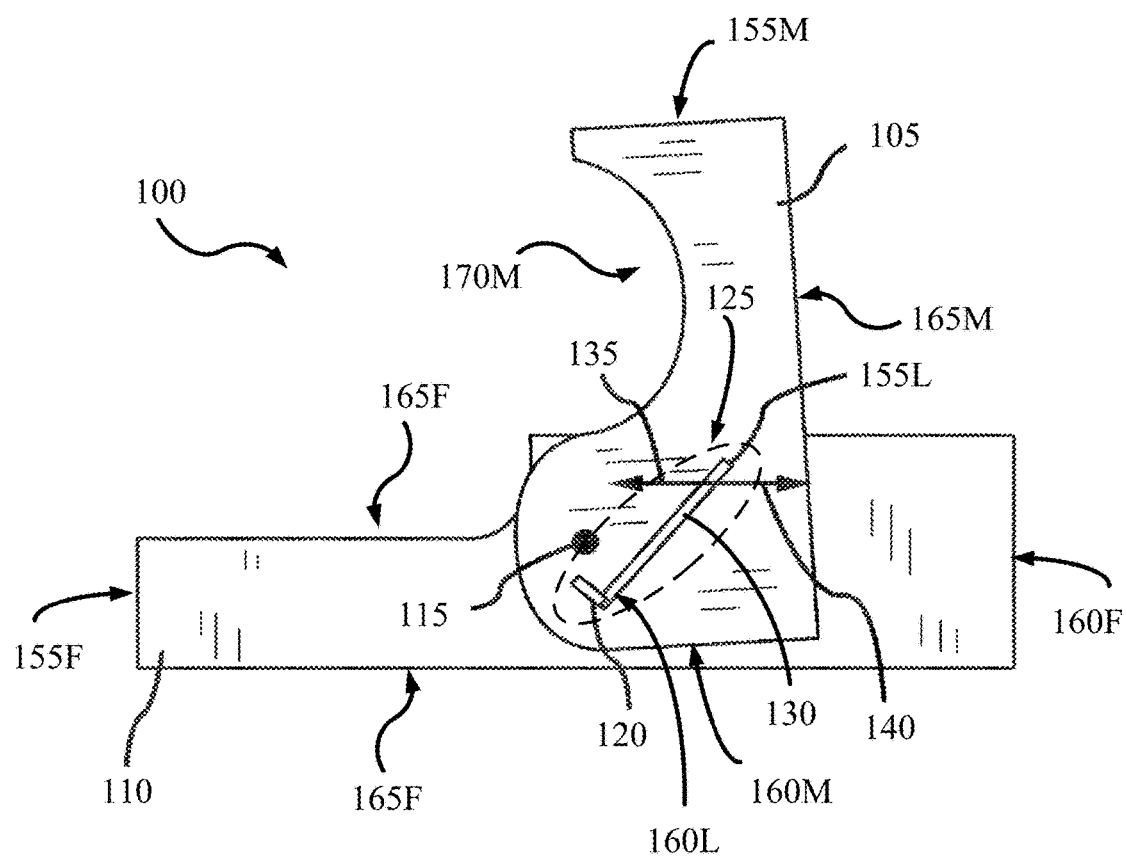
FIG. 4 illustrates a switchable prehensor in voluntary open mode, in the open position, according to some embodiments of the present disclosure.

FIGS. 3 and 4 illustrate a terminal device 100 with its switchable biasing mechanism 125 positioned such that the terminal device 100 is configured for the VO mode of operation. In VO mode, the distal end 155L of the lever 130 of the switchable biasing mechanism 125 is in its second position where the distal end 155L of the lever 130 is positioned above the first connector 115 or towards the dorsal side 165F of the fixed digit 110. Further, while the lever 130 of the switchable biasing mechanism 125 is in the second position, when the first force-generating mechanism 135 provides a passive force to the distal end 155L of the lever 130 that is greater than the active force applied to the distal end 155L of the lever 130 by the second force-generating mechanism 140, the terminal device 100 will remain in the closed position as shown in FIG. 3. However, once the active force provided to the distal end 155L of the lever 130 by the second force-generating mechanism 140 exceeds the passive force provided by the first force-generating mechanism 135, the distal end 155L of the lever 130 will move towards the proximal end 160F of the fixed digit 110, resulting in the movement of the moveable digit 100 to the open position of the terminal device 100, as shown in FIG. 4.

Referring again to FIG. 1, for a terminal device 100 in VC mode, when the lever 130 is in the first position (directed towards the palmar side 170F of the fixed digit 110) and when the passive force generated by the first force-generating mechanism 135 is less than the active force generated by the second force-generating mechanism 140, and the terminal device 100 is in the closed position, the lever 130 is oriented at an angle, hereinafter referred to as the "total swing angle", of about 45° from the second axis 150, where the reference point for 0° is when the lever 130 is substantially parallel with the second axis 150 and the distal end 155L of the lever 130 is directed substantially towards the proximal end 160F of the fixed digit 110, and 90° is when the lever 130 is substantially perpendicular to the second axis 150 and the distal end 155L of the lever 130 is directed substantially towards the palmar side 170F of the fixed digit 110. Thus, when in the closed position during VC mode, the lever 130 may be oriented at a total swing angle between about 0° and about 180°, between about 10 and about 170°, between about 20 and about 160°, between about 30 and about 150°, between about 40 and about 140°, between about 50 and about 130°, between about 60 and about 120°, between about 70 and about 110°, or between about 80 and about 100°.

Referring again to FIG. 2, for a terminal device 100 in VC mode, when the lever 130 is in the first position (directed towards the palmar side 170F of the fixed digit 110) and when the passive force generated by the first force-generating mechanism 135 is larger than the active force generated by the second force-generating mechanism 140, and the terminal device 100 is in the open position, the lever 130 may be oriented at a total swing angle of about 45° from the second axis 150, where the reference point for 0° is when the lever 130 is substantially parallel with the second axis 150 and the distal end 155L of the lever 130 is substantially directed towards the distal end 155F of the fixed digit 110, and 90° is when the lever 130 is substantially perpendicular to the second axis 150 and is directed towards the palmar side 170F of the fixed digit 110. Thus, when in the open position during VC mode of operation, the lever 130 may be oriented at a total swing angle of between about 0° and about 180°, between about 10 and about 170°, between about 20 and about 160°, between about 30 and about 150°, between about 40 and about 140°, between about 50 and about 130°, between about 60 and about 120°, between about 70 and about 110°, or between about 80 and about 100°.

Referring again to FIG. 3, for a terminal device 100 in VO mode, when the lever 130 is in the second position (directed towards the dorsal side 165F of the fixed digit 110) and when the passive force generated by the first force-generating mechanism 135 is more than the active force generated by the second force-generating mechanism 140, and the terminal device is in the closed position, the lever 130 may be oriented at a total swing angle of about 45° from the second axis 150, where the reference point for 0° is when the lever 130 is substantially parallel with the second axis 150 and the distal end 155L of the lever 130 is directed substantially towards the distal end 155F of the fixed digit 110, and 90° is when the lever 130 is substantially perpendicular to the second axis 150 and the distal end 155L of the lever 130 is directed substantially towards the dorsal side 165F of the fixed digit 110. Thus, when in the closed position during VO mode, the lever 130 may be oriented at a total swing angle between about 0° and about 180°, between about 10 and about 170°, between about 20 and about 160°, between about 30 and about 150°, between about 40 and about 140°, between about 50 and about 130°, between about 60 and about 120°, between about 70 and about 110°, or between about 80 and about 100°.

Referring again to FIG. 4, for a terminal device 100 in VO mode, when the lever 130 is in the second position (directed towards the dorsal side 165F of the fixed digit 110) and when the passive force generated by the first force-generating mechanism 135 is less than the active force generated by the second force-generating mechanism 140, and the terminal device is in the open position, the lever 130 may be oriented at a total swing angle of about 45° from the second axis 150, where the reference point for 0° is when the lever 130 is substantially parallel with the second axis 150 and the distal end 155L of the lever 130 is directed substantially towards the proximal end 160F of the fixed digit 110, and 90° is when the lever 130 is substantially perpendicular to the second axis 150 and the distal end 155L of the lever 130 is directed substantially towards the dorsal side 165F of the fixed digit 110. Thus, when in the open position during VO mode, the lever 130 may be oriented at a total swing angle between about 0° and about 180°, between about 10 and about 170°, between about 20 and about 160°, between about 30 and about 150°, between about 40 and about 140°, between about 50 and about 130°, between about 60 and about 120°, between about 70 and about 110°, or between about 80 and about 100°.

Thus, the amount of arc that the distal end 155L of the lever 130 sweeps when the lever 130 starts at from a passive state, either in the closed position or the open position, to a fully actuated state caused by the applying of an active force to the distal end 155L of the lever 130 may be determined by adding the swing angle of the lever 130 when in the passive state to the swing angle of the lever 130 when in the actuated state. Thus, the sum of the passive swing angle and the actuated swing angle is the angle of rotation described above.

The second connector 120 may be a cylindrical structure, such as a pin, a nail, a screw, a rod, a post, and/or a rivet. The second connector 120 may be directly connected to the first connector 115 or the second connector 120 may be separated from the first connector 115 by a space and/or a gap. The lever 130 of the switchable biasing mechanism 125 may be reversibly switched from its first position (e.g. palmar side 170F of the fixed digit 110) to its second position (e.g. dorsal side 165F of the fixed digit 110) by moving the distal end 155L of the lever 130 in a plane that is substantially perpendicular and/or non-parallel to the first axis 145, the second axis 150, and/or the plane defined by the fixed digit 110 and/or the moveable digit 105.

In some embodiments of the present disclosure, a terminal device 100 may also include a first force-generating mechanism 135 that applies a passive force to the distal end 155L of the lever 130 in a direction substantially towards the distal end 155F of the fixed digit 110, and a second force-generating mechanism 140 that applies an active force to the distal end 155L of the lever 130 in a direction substantially opposite to the direction of the passive force, for example, towards the proximal end 160F of the fixed digit 110. In some embodiments of the present disclosure, the first force-generating mechanism 135 may be an elastic band and/or elastic cord, and the second force-generating mechanism 140 may be a non-elastic cord and/or non-elastic cable such that the user actuates the non-elastic cord and/or non-elastic cable to apply the active force to the distal end 155L of the lever 130. When the lever 130 is in the first position (e.g. corresponding to the VC mode of operation as shown in FIGS. 1 and 2) and the second force-generating mechanism 140 (e.g. a cable actuated by the user) applies an active force that is greater than the passive force, the distal end 155L of the lever 130 is pulled in a proximal direction, towards the proximal end 160F of the fixed digit 110. In some embodiments of the present disclosure, this proximally-directed movement of the distal end 155L of the lever 130 results in moving the distal end 155L of the lever from a position on the distal side of the first connector 115 to the proximal side of the first connector 115. This motion of the distal end 155L of the lever 130 results in movement of the distal end 155M of the moveable digit 105 towards the distal end 155F of the fixed digit 110, thereby closing the terminal device 100. When the lever 130 is in the second position (e.g. positioned towards the dorsal side 165F of the fixed digit 110 corresponding to the VO mode of operation as shown in FIGS. 3 and 4) and the second force-generating mechanism 140 (e.g. a cable actuated by the user) applies an active force that is greater than the passive force, the distal end 155L of the lever 130 is again pulled in a proximal direction, towards the proximal end 160F of the fixed digit 110. This proximally-directed movement of the distal end 155L of the lever 130 results in movement of the distal end 155L of the lever from a position on the distal side of the first connector 115 to the proximal side of the first connector 115. This motion of the distal end 155L of the lever 130 in turn results in movement of the distal end 155M of the moveable digit 105 away from the distal end 155F of the fixed digit 110, thereby opening the terminal device 100.

In some embodiments of the present disclosure, the passive force applied by the first force-generating mechanism 135 and the active force applied by the second force-generating mechanism 140 may be directed in substantially opposite directions. For example, the passive force may be applied in a direction that is substantially parallel with the second axis 150 of the fixed digit 110 (e.g. the longitudinal axis of the fixed digit) and towards the distal end 155F of the fixed digit 110, whereas the active force may be applied in a direction also substantially parallel with the second axis 150 of the fixed digit 110 and towards the proximal end 160F of the fixed digit 110.

In some embodiments of the present disclosure, the first force-generating mechanism 135 for applying a passive force may be at least one of a spring, an elastic cord, a pressurized cylinder, and/or any other suitable stretchable and/or elastic member capable of storing mechanical energy. A spring may include at least one of an extension spring, a compression spring, a torsion spring, a clock spring, a power spring, and/or a constant force spring. Materials of construction may be selected as needed, depending on specific design criteria, these selections being known to those skilled in the art with examples including plastic and metal. Examples of materials of construction for elastic cords (e.g. the first force-generating mechanism) include, but are not limited to, plastic materials, elastic materials, and silastic materials. Rope, cord, and fibers may also be selected as appropriate for a specific design need, if they provide some degree of elasticity. In general, the first force-generating mechanism 135 for applying a passive force includes an elastic mechanical element that can be either stretched and/or compressed from a first state in which the mechanical element has zero and/or a substantially low stored mechanical energy, to a second state wherein the mechanical element contains more stored mechanical energy then when the mechanical element is in the first state. The stored energy provides the passive force that moves the moveable digit 105 back to a static equilibrium state, once the passive force exceeds the active force. In some embodiments of the present disclosure, the magnitude of this passive biasing force may be adjusted. This may be accomplished by changing the attachment point of the first force-generating mechanism 135 (e.g. an elastic cord, tension cord, etc.) to the distal end 155L of the lever 130 to effectively alter the length of the lever 130, and/or by changing where the first force-generating mechanism 135 is anchored, and/or by changing the internal force-generating characteristics of the first force-generating mechanism 135 itself, for example by increasing and/or decreasing the force generated by changing an internal spring force, a working fluid pressure, and/or other relevant characteristic applicable to the first force-generating mechanism 135 used.

The first force-generating mechanism 135 may provide either a "pulling" passive force to the distal end 155L of the lever 130 and/or a "pushing" passive force to the distal end 155L of the lever 130. Thus, in some embodiments of the present disclosure, a first force-generating mechanism 135 may provide a pulling passive force utilizing an elastomer element such as at least one of a tension cord, an elastic cord, bungee cord, a rubber band, and/or a tension spring. In some embodiments of the present disclosure, a first force-generating mechanism 135 may provide a pulling passive force utilizing a mechanical arrangement that provides a constant-force and/or constant-power spring (e.g. a "clock spring"). In some embodiments of the present disclosure, a first force-generating mechanism 135 for providing a pulling force may include at least one of a pneumatic device, a hydraulic device, a McKibben actuator, a solenoid, an electromagnetic device, and/or reactive materials configured to provide a pulling force and/or a tensile force. In some embodiments of the present disclosure, a first force-generating mechanism 135 for providing a pushing passive force may include at least one compression spring configured within a piston-like arrangement similar to vehicle shock absorbers and/or within a telescoping tube (e.g. such as those used to support and retain toilet paper rolls in a dispenser). In some embodiments of the present disclosure, the "pulling" first force-generating mechanisms 135 listed above may be configured to act on a rigid member that provides a push force, thus converting the "pulling" first force-generating mechanism 135 to a "pushing" first force-generating mechanism 135.

A second force-generating mechanism 140 for applying an active force may include at least one of a rope, a cord, a fiber, a wire, a filament, and/or any other flexible, yet substantially inelastic, cord-like member. Unlike the first force-generating mechanism 135 for applying a passive force, the second force-generating mechanism 140 for applying an active force may have little, if any, ability to store energy. Thus, the second force-generating mechanism 140 for applying an active force may be essentially inelastic. This is because, for efficient operation, body movements used to activate the prosthetic terminal device 100 should translate into actual displacement of the device, without stretching the second force-generating mechanism; e.g. the control line, wire, and/or cable. Otherwise, the user may need to make excessive or unnatural movements to compensate for the inefficiencies of the system. Thus, in some embodiments of the present disclosure, the second force-generating mechanism 140 for applying an active force may have zero elasticity and/or some low amount of elasticity. The active force may be generated by the user such that the active force is transferred to the second force-generating mechanism 140 such that when the active force exceeds the passive force, the terminal device is actuated from the open position to the closed position and/or from the closed position to the open position. However, non-human actuators may also generate the active force that is transferred by the second force-generating mechanism 140 with examples including at least one of a hydraulic device, a pneumatic device, an electromechanical device, piezoelectric device, a device utilizing a reactive polymer, and/or a magnetostrictive device.

The passive forces (with a first passive force for the VC mode and a second passive force for the VO mode) applied to the terminal device 100 may be varied. For example, the ratio of the passive force (the VC passive force) applied to the distal end 155L of the lever 130 while the terminal device 100 is open during VC mode, to the passive force (the VO passive force) applied to the lever 130 while the terminal device is closed during VO mode may be about equal to one. Hereinafter, this ratio of passive forces when the terminal device 100 is in its two respective unactuated, passive states is referred to as the VC/VO force ratio. In some embodiments of the present disclosure, the VC/VO force ratio may be less than about one. In some embodiments of the present disclosure, the VC/VO force ratio may be about 1.0, about 0.9, about 0.8, about 0.7, about 0.6, about 0.5, about 0.4, about 0.3, about 0.2, and/or about 0.1. In some embodiments of the present disclosure, the VC/VO force ratio may be greater than about one. In some embodiments of the present disclosure, the VC/VO force ratio may be about 1.0, about 1.1, about 1.2, about 1.3, about 1.4, about 1.5, about 1.6, about 1.7, about 1.8, about 1.9, or about 2.0. Assuming the length of the lever 130 does not change, the VO passive force should generally be larger than VC passive force to generate useful pinch force. Some of the embodiments described below in reference to FIGS. 9-12 provide features and relationships that uniquely enable embodiments of the present terminal device to set and/or adjust the VC/VO force ratio.

In some embodiments of the present disclosure, the VC passive force generated by the first force-generating mechanism 135 (e.g. an elastic cord) may be, at its lowest setting, between about 2 $lb_f$ and about 5 $lb_f$ of cable tension to ensure the user preserves physiological proprioception and that the actuating cable, the second force-generating mechanism 140, does not go slack. This also insures that the actuating cable is pulled back through the terminal device 100 (e.g. through a housing of the terminal device 100) and may be cycled without becoming "stuck" by friction of the cable moving through the housing. The VO passive force, at its lowest setting, may be selected to ensure that the terminal device 100 closes fully, and maintains the maximum VO passive force possible, while still allowing the user to operate and cycle the terminal device 100. A desired VC/VO force ratio may be achieved by varying the elasticity of the first force-generating mechanism 135 (e.g. tension cord) for providing the passive force, varying the length of the lever 130, changing the position of the proximal end 160L of the lever 130 relative to the second axis 150 of the fixed digit 110, and/or by changing the position of the proximal end 160L of the lever 130 on the palmar-dorsal axis perpendicular to the second axis 150 of the fixed digit 110. In some embodiments of the present disclosure, VO passive force>VC passive force>about 2 $lb_f$ to about 5 $lb_f$ cable tension. In some embodiments of the present disclosure, VC passive force>VO passive force>about 2 $lb_f$ to about 5 $lb_f$ cable tension.

Figure 5:
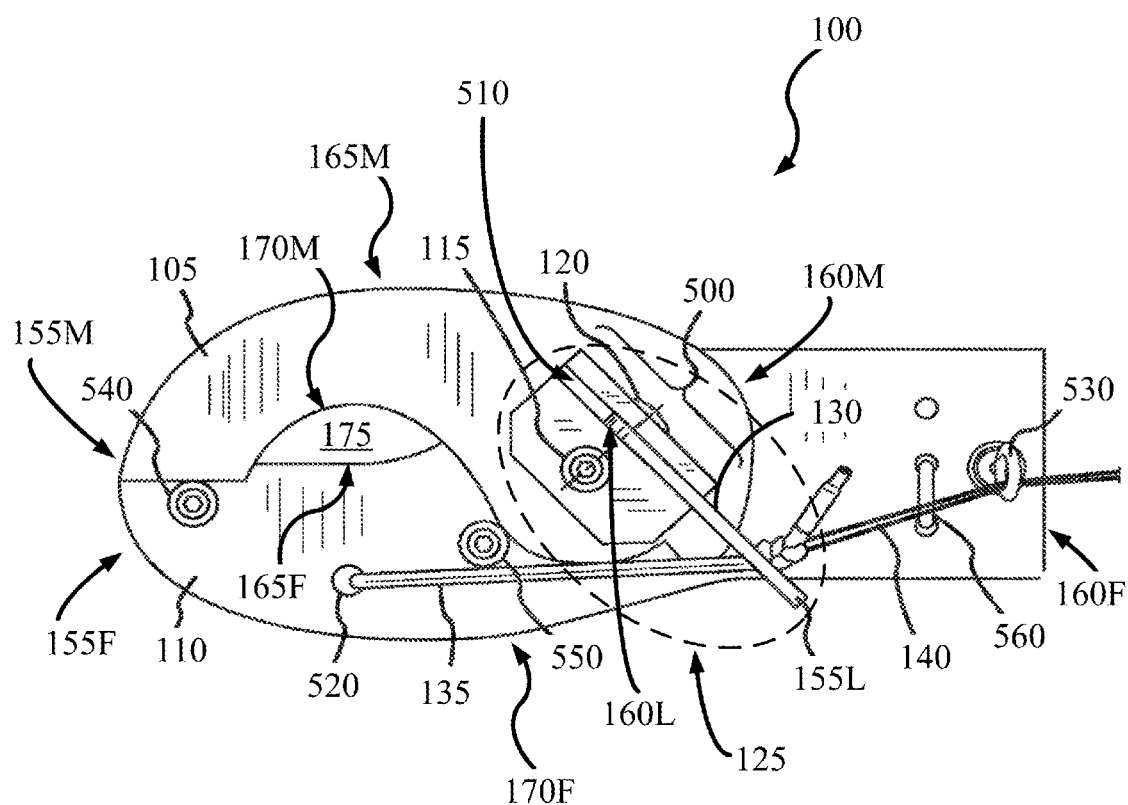
FIG. 5 illustrates a switchable prehensor in voluntary closed mode, in the closed position, according to some embodiments of the present disclosure.

FIG. 5 illustrates a switchable terminal device 100 positioned in the VC mode of operation (with the distal end 155L of the lever 130 in the first position, on the palmar side 170F of the fixed digit 110) in the closed position, where the user has actuated the second force-generating mechanism 140 in the form of a cable, which has pulled the distal end 155L of the lever, resulting in the movement of the distal end 155M of the moveable digit 105 towards the distal end 155F of fixed digit 110. Thus, FIG. 5 illustrates the terminal device in the completely closed position. The final closed position in this example is determined by a first stop 540 positioned near the distal end 155F of the fixed digit 110. As long as the user continues to apply a sustained active force to the second force-generating mechanism 140 (e.g. the cable), the active force will be transferred to the lever 130, which will result in the distal ends (155F and 155M) of the opposing digits (110 and 100 respectively) maintaining an opposing pinch force.

As in previous examples, the terminal device 100 shown in FIG. 5 also includes a moveable digit 105 moveably connected to a fixed digit 110 by a first connector 115. In this example, both the moveable digit 105 and fixed digit 110 are manufactured from plastic. Specifically, the moveable digit 100, the fixed digit 110, and the first connector 115 are made from PVC; e.g. in a sheet form. The terminal device 100 includes a switchable biasing mechanism 125 having a lever 130 with a proximal end 160L attached to a second connector 120, which is positioned in a block of PVC. This block is affixed to the moveable digit 105 and is referred to herein as a lever guide 500 because the lever guide 500 contains a first channel 510 configured to anchor the proximal end 160L of the lever 130 to the lever guide 500 and configured for at least a portion of the length of the lever 130 to fit within the first channel 510 to hold the lever 130 securely in place, especially when the passive force and active force are applied to the distal end 155L of the lever. Thus, among other things, the lever guide provides structural support to the lever 130 and a robust solid connecting/transition piece from the forces applied to the lever 130 to the moveable digit 105. This example of a terminal device 100 includes a first stop 540 and a second stop 550, both manufactured from nylon. The first stop 540 limits the movement of the moveable digit 105 during VC mode and/or VO mode of operation by physically preventing the distal end 155M of the moveable digit 105 from moving too far past the distal end 155F of the fixed digit in the palmar direction. The second stop 550 limits the movement of the moveable digit 105 during VC mode and/or VO mode of operation by physically preventing the proximal end 160M of the moveable digit 105 from over-rotating in the distal direction and/or prevents the terminal device 100 from opening too far. In this example, the first connector 115 and the second connector 120 are constructed of stainless fasteners and/or rivets, and the lever 130 is made from stainless steel. The first force-generating mechanism 135 is constructed using a bungee cord (e.g. a tension cord).

Referring again to FIG. 5, the second force-generating mechanism 140 is an inelastic cable constructed of Spectra® cord. The proximal end (not shown) of this cable is body actuated by the user. A portion of the distal end 155C of the second force-generating mechanism 140 (e.g. cable) passes through a cable guide 530 and terminates and is attached to the distal end 155L of the lever 130. The cable guide 530 helps to maximize user efficiency by minimizing the body's linear displacement and/or movement needed to move the distal end 155M of the moveable digit 105 a certain defined distance, as needed for a particular device and design. Configuring the second force-generating mechanism 140, e.g. cable, to move through this point establishes symmetry between the VO/VC modes and ensures the cable excursion starting positions are identical for both modes. This in turn helps to minimize the length of cable required. Alternatively, a terminal device 100 may be constructed without a cable guide 530 and alternatively the cable may be effectively held in the spatial position shown in FIG. 5 by a separate element (not shown) external to the terminal device 100. FIG. 5 illustrates a first force-generating mechanism 135 in the form of a tension cord (or bungee cord), with a first end of the tension cord, the proximal end, terminating at the distal end 155L of the lever 130 and a second end, the distal end, terminating at and/or near the distal end 155F of the fixed digit 110. In this example, the terminal device 100 has a hole drilled through the distal end 155L of the lever 130 and the first end of the tension cord is passed through this hole and knotted to prevent the tension cord from slipping back through the hole. This hole is referred to as a securement point 520. In this example, the securement point 520 is a hole drilled through the fixed digit 110, in the proximal portion of the fixed digit 110 and/or near the distal end 155F of the fixed digit 110. It may be preferred to use a low-friction coefficient securement point 520 and/or a pulley to minimize drag on the tension cord at the securement point 520 for more efficient operation, to reduce frictional wear, and to extend the lifespan of the tension cord. In the example of FIG. 5, the tension cord is passed through the securement point 520 (e.g. a hole) and redirected (not shown) back to the proximal end 160F of the fixed digit 110 where it is secured in place at an anchor point 560. In this example, the terminal end of the tension cord is passed through the tension anchor point 560, which is constructed of two holes drilled through the fixed digit 110, and tied off (not shown).

Referring again to FIG. 5, the proximal end 160L of the lever 130 is secured to the lever guide 500 at a second connector 120, which in this example is a metal pin. Both the first connector 115 and the second connector 120 pass through the lever guide 500. In this example, the lever guide 500 is a plastic monolith (or body) with the first channel 510, a groove, machined into it. The lever guide 500 is fixed securely to the moveable digit 105, either by the tension force applied by the first connector 115, and/or by a suitable adhesive applied to the opposing faces of the lever guide 500 and the moveable digit 105. The second connector 120, e.g. a metal pin, is secured through a hole that has been drilled through the lever guide 500, through the proximal end 160L of the lever 130, and continues into and terminates within the lever guide 500. In this example, this hole contains the second connector 120 and is positioned substantially perpendicular to the first connector 115, e.g. the rivet, and enables the lever 130 to be rotated around a pivot point created by the second connector 120 in a plane that is substantially orthogonal to the plane created by the moveable digit 105 and the fixed digit 110. FIG. 5 illustrates the distal end 155L of the lever 130 positioned towards the palmar side of the terminal device 100, the first position (e.g. positioned towards the palmar side 170F of the fixed digit 130) corresponding to the VC mode of operating the terminal device 100.

Figure 6:
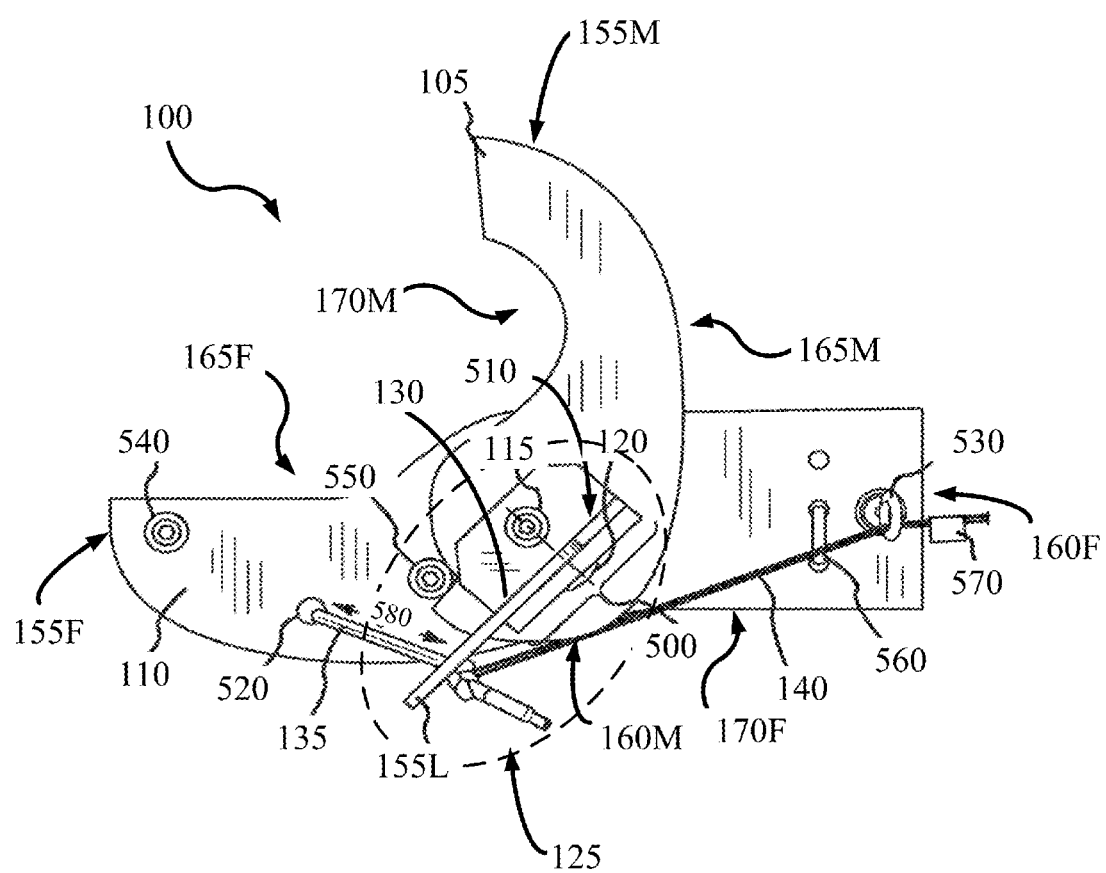
FIG. 6 illustrates a switchable prehensor in voluntary closed mode, in the open position, according to some embodiments of the present disclosure.

FIG. 6 illustrates the terminal device 100 shown in FIG. 5, in this case configured for the passive open position during VC operation. Relative to FIG. 5, the user has released the active force applying tension to the second force-generating mechanism 140, e.g. the cable. Thus, a flag 570 positioned on the cable proximal to the anchor point 560 illustrates the cable starting position in the neutral state (for comparison to FIG. 7). A second characteristic metric illustrated by FIG. 6 is the VC passive length 580 of the first force-generating mechanism 135, e.g. the tension cord, in the absence of an active force. The VC passive length 580, is one factor that defines the passive force applied by the tension cord when the device is in voluntary close mode. FIG. 6 also illustrates that the amount of allowable movement by the moveable digit 105 and the angle of rotation of the terminal device 100 is determined at least partly by the position of the second stop 550 on the fixed digit 110.

Figure 7:
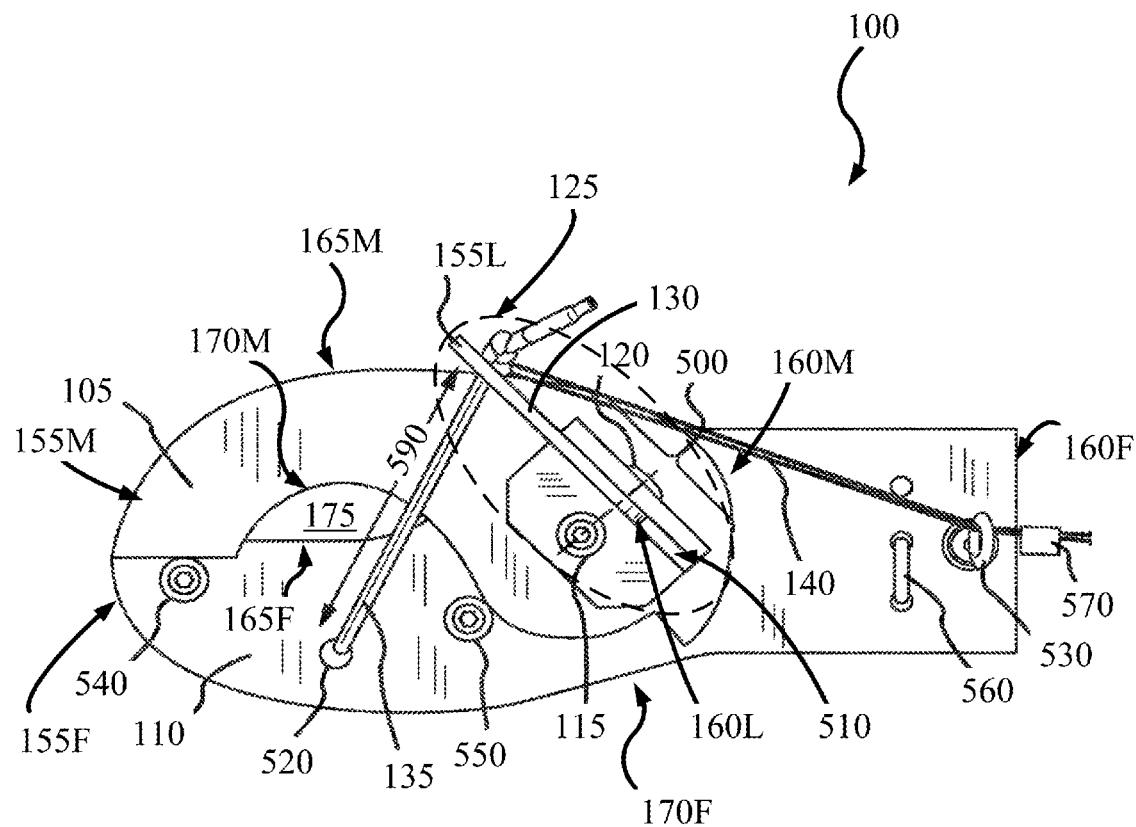
FIG. 7 illustrates a switchable prehensor in voluntary open mode, in the closed position, according to some embodiments of the present disclosure.

FIG. 7 illustrates the terminal device 100 previously illustrated in FIGS. 5 and 6, but now for the terminal device configured for VO mode of operation, while in the passive closed position, with the lever 130 in its second position (e.g. on the dorsal side 165F of the fixed digit 110). The user has rotated the distal end 155L of the lever 130 around its pivot point, the second connector 120, from the first position (on the palmar side 170F of the fixed digit 110) to the second position (on the dorsal side 165F of the fixed digit 110). The terminal device 100 is in the passive state, because the user has not applied an actuating, active force to the second force-generating mechanism 140, e.g. the cable. Note the position of the flag 570, which is in substantially the same position as shown in FIG. 6 for the passive state while in the VC mode. This illustrates that the objective of providing an easily switchable terminal device, wherein the second force-generating mechanism 140 resting position, the cable resting position, is the essentially the same regardless of whether the terminal device 100 is in the VO mode of operation, or in VC mode of operation, has been met. This is because of the careful selection of the geometric relationships between the fixed digit 110 and the moveable digit 105, the length of the lever 130, and the positioning of the distal end 155L of the lever 130 on the plane defined by the fixed digit 110 and the moveable digit 105 and relative to the point defined by the first connector 115.

FIG. 7 illustrates the passive length of the first force-generating mechanism 135, the tension cord, in the absence of an active force, referred to herein as the VO passive length 590. A comparison of the VO passive length 590 of FIG. 7 to the VC passive length 580 of FIG. 6 shows the VO passive length 590 is longer than the VC passive length. In this example, because the first force-generating mechanism 135, the tension cord is an elastic band, the longer VO passive length for the tension cord translates to a higher passive force applied to the distal end 155L of the lever 130, which means the active force that the user needs to apply to move the lever 130 to overcome this force is also higher.

Figure 8:
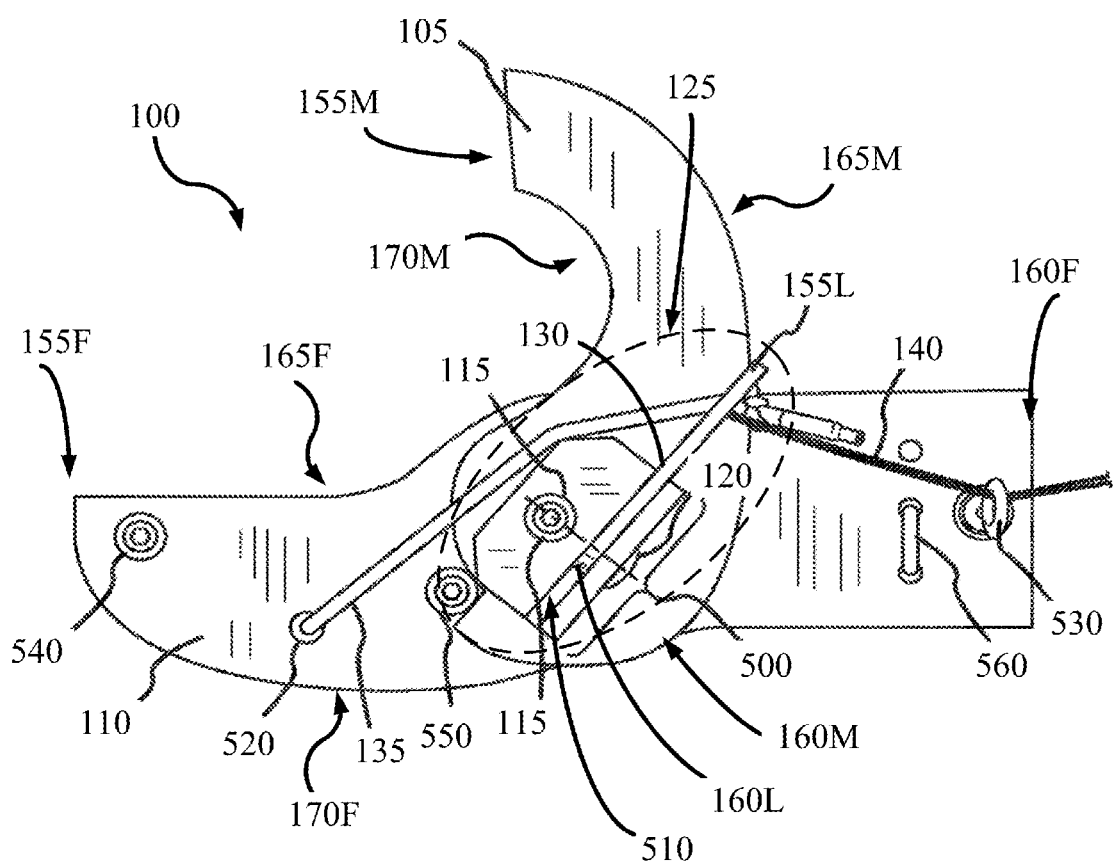
FIG. 8 illustrates a switchable prehensor in voluntary open mode, in the open position, according to some embodiments of the present disclosure.

FIG. 8 illustrates the terminal device 100 previously described for FIGS. 5-8 for the situation where the user has applied an active force greater than the passive force, by actuating the second force-generating mechanism 140, e.g. the cable, in a proximal direction substantially parallel to the first (longitudinal) axis 145 of the fixed digit 110. In this case, the active force has pulled the distal end 155L of the lever 130 from a distal position to a proximal position, in the process moving the distal end 155M of the moveable digit 105 through an angle of rotation of about 90° until the movement is stopped by the second stop 550. Releasing the active force and tension from the cable allows the passive force generated by the tension cord to pull the distal end 155L of the lever 130 back in the distal direction, such that the terminal device 100 returns to the passive closed position. So, in summary, the passive force applied by the tension cord while the terminal device 100 is closed during VO mode is greater than the active force that the user needs to apply to move the terminal device 100 from the open position to the closed position while in the VC mode of operation. Thus, the objective of this disclosure to provide a switchable terminal device, wherein when the terminal device is in VC mode, the force needed to open the device is relatively low, while still providing a comparably strong closing force when switched to the VO mode is met.

Figure 9:
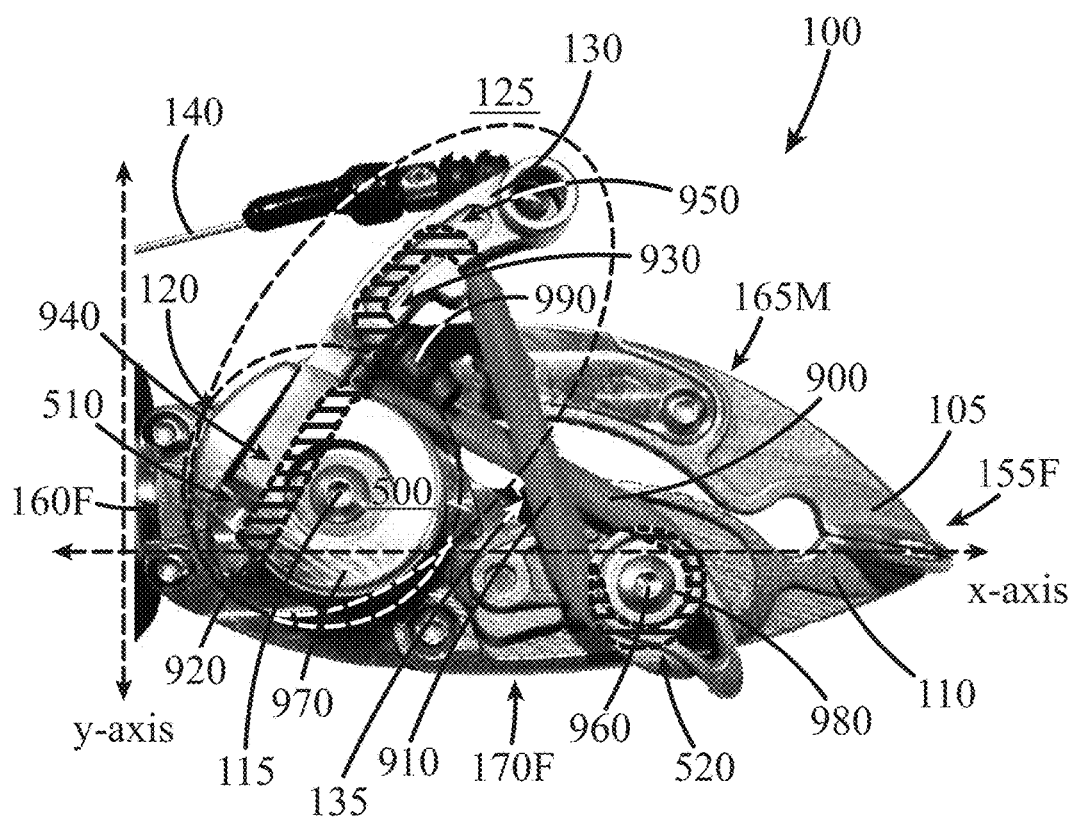
FIG. 9 illustrates a switchable prehensor in voluntary open mode, in the closed position, according to some embodiments of the present disclosure.

FIGS. 9-12 illustrate another example of a switchable terminal device 100, that may be switched at will by the user from a VC mode of operation to a VO mode of operation. Referring to FIG. 9, the terminal device 100 includes a moveable digit 105 rotatably connected to a fixed digit 110 by a first connector 115. As shown in this example, the first connector 115 may be a pin, however, the first connector 115 may include at least one of a pin, a screw, a rivet, a nail, a rod, a post, and/or any other similar mechanical device for connecting the moveable digit 105 to the fixed digit 110. The terminal device 100 also includes a switchable biasing mechanism 125. In this example, the switchable biasing mechanism 125 includes a lever guide 970 of which a portion is substantially in the shape of a drum with the first connector 115 (e.g. pin) positioned substantially in the center of the drum. In other words, the first connector 115 (e.g. pin) may be aligned along a center axis of the drum and pass through the center of the drum. In this example, the drum (lever guide 970) is substantially in the shape of a cylindrical block of material with the first connector 115 (e.g. pin) passing through the center axis of the cylindrical block of material, where the center axis is substantially perpendicular to the xy-plane.

The lever guide 970 shown in FIG. 9 is referred to herein as "substantially in the shape of cylinder" because at least 180 degrees of its outer circumference is substantially circular in shape. The remaining outer circumference of the lever guide 970 may also have a circular shape, however, as shown in FIG. 9, the remaining circumference may be in a shape other than circular/cylindrical. Thus, the lever guide 970 may be divided into a first portion that is substantially circular in shape, and a second portion that may or may not be substantially circular in shape. The circular portion of the lever guide 970 may be substantially circular in shape to provide a low friction, smooth guide and/or to smoothly interface with the first force-generating mechanism 135, in this example, at least one of a tension cord, elastic cord, bungee cord, rubber band, etc. Thus, the circular shape of the first portion of the lever guide 970 may help minimize frictional wear of the first force-generating mechanism 135, the tension cord, as the user repeatedly actuates the second force-generating mechanism 140, in this example, a substantially inelastic cable, cord, wire, string, rope, etc., to pull and release the distal end 155L of the lever 130, which in turn stretches and relaxes the first force-generating mechanism 135, the tension cord. Minimizing frictional wear may extend the life of the tension cord. Thus, in this example of a terminal device 100, the switchable biasing mechanism 125 includes the lever guide 500 having a first portion that is a cylindrically-shaped (e.g. drum) lever guide 970 with the first connector 115 positioned through the center of the drum. In addition, this example of a switchable biasing mechanism 125 includes the reversibly switchable lever 130 having a proximal end 160L moveably connected to the lever guide 500 and attached to the lever guide 500 by a second connector 120. In addition, at least a portion of the length of the lever 130 is positioned within a first channel 510 located in the second portion (in this case, substantially non-cylindrical portion) of the lever guide 500. The first force-generating mechanism 135 of this example, a tension cord has a first end 920 and a second end 930 where the first end 920 is secured within a second channel 940 positioned within a portion of the lever guide 500 and the second end 930 is secured within a third channel 950 positioned within a portion of the distal end 155L of the lever 130.

FIG. 9 illustrates the switchable terminal device 100 when in a non-actuated state, in this case in the closed position while configured for the voluntary open (VO) mode of operation. The first cylindrical portion of the lever guide 500 (e.g. drum) is positioned towards the distal end of the terminal device 100 and the second portion of the lever guide 500 is positioned towards the proximal end of the terminal device 100. The second portion (e.g. non-cylindrical) of the lever guide 500 provides the volume and/or physical mass needed to correctly position the lever 130 relative to the first connector 115 (e.g. a pin). This volume and/or mass of the second portion of the lever guide 500 provides the space needed for the first channel 510 to be positioned within the second portion (in this example, the substantially non-cylindrical portion) of the lever guide 500. The first channel 510, in the form of a channel or groove, contains a portion of the proximal end 160L of the lever 130. Further, the proximal end 160L of the lever 130 is moveably and/or rotatably secured within the first channel 510 by the second connector 120. The second connector 120 may include a pin, nail, screw, rivet, rod, or post and/or any other suitable mechanical element for securing the proximal end 160L of the lever 130 to the lever guide 500. In addition, the second, non-cylindrical portion of the lever guide 500 also provides the mass and volume of material needed to provide a second channel 940 positioned within the lever guide 500. In this example, the second channel 940 is positioned in the lever guide 500 below the first channel 510. The second channel 940 provides a securement point for a first end 920 and/or portion of the first force-generating mechanism 135, e.g. the tension cord. Because of the location of the second channel 940, it is not directly visible in FIG. 9 and its position is indicated by the position of the first force-generating mechanism 135, the first end 920 of the tension cord positioned within the second channel 940 (the dashed/hash-marked portion of the tension cord).

The first force-generating mechanism 135, the tension cord, includes a first segment 900 that includes the first end

920. The tension cord also includes a second segment 910 that includes the second end 930. The first end 920 and a portion of the first segment 900 are positioned within the second channel 940, which is contained within the second portion of the lever guide 500. The first end 920 of the first segment 900 of the first force-generating mechanism 135, the tension cord, is physically secured within the second channel 940 using any suitable means, with examples including nails, screws, rivets, staples, compression fittings, glue, and/or adhesive. The first segment 900 of the first force-generating mechanism 135, the tension cord, extends from this point of attachment in the lever guide 500, passes through the second channel 940, and exits the second channel 940 at or near a portion of the outer circumference of the first circular portion of the lever guide 970. The lever guide 970 may contain a channel and/or groove around its outer circumference (not shown) to insure that the first segment 900 of the tension cord remains in position on the outer perimeter or edge of the lever guide 970 (e.g. drum), especially when the user actuates the lever 130 of the switchable biasing mechanism 125.

Still referring to FIG. 9, the first segment 900 of the first force-generating mechanism 135, the tension cord, then traverses the distance between the proximally positioned lever guide 970 (relative to the x-axis shown in FIG. 9) to a distally positioned securement point 520 positioned on a distal portion of the fixed digit 110. In the example of FIG. 9, the securement point 520 includes a circular shaped pulley 980 rotatably connected to the fixed digit 110 by a third connector 960 in the form of a cylindrical post or rod. Thus, the first segment 900 of the first force-generating mechanism 135, the tension cord, extends from the lever guide 970 to contact and pass around the outer circumference of the rotatable pulley 980, at which point the second segment 910 of the first force-generating mechanism 135 begins, which then traverses the distance between the rotatable pulley 980 to connect with the distal half and/or distal end 155L of the lever 130. The second segment 910 of the first force-generating mechanism 135, the tension cord, then enters a third channel 950 positioned within the lever 130 along its longitudinal axis. The third channel 950 has a first opening positioned within the distal half and/or at the distal end 155L of the lever 130. The third channel 950 then passes through the lever 130 along its longitudinal axis to terminate at or near the proximal end 160L of the lever 130. Thus, the second segment 910 of the tension cord enters the lever 130 through the first opening, passes through the third channel 950, where the second end 930 of the tension cord terminates at or near the proximal end 160L of the lever 130. As shown in the example of FIG. 9, the second end of the first force-generating mechanism 135, the tension cord, passes through a second opening positioned at or near the proximal end 160L of the lever 130 and is secured to the lever 130 by a widened portion of the tension cord, referred to herein as a stopper 990. However, it should be understood, that other methods and/or elements may be used to secure the second end 930 of the tension cord 500 to the lever 130 with examples including any suitable means, such as nails, screws, staples, compression fittings, glue, and/or adhesive.

Figure 10:
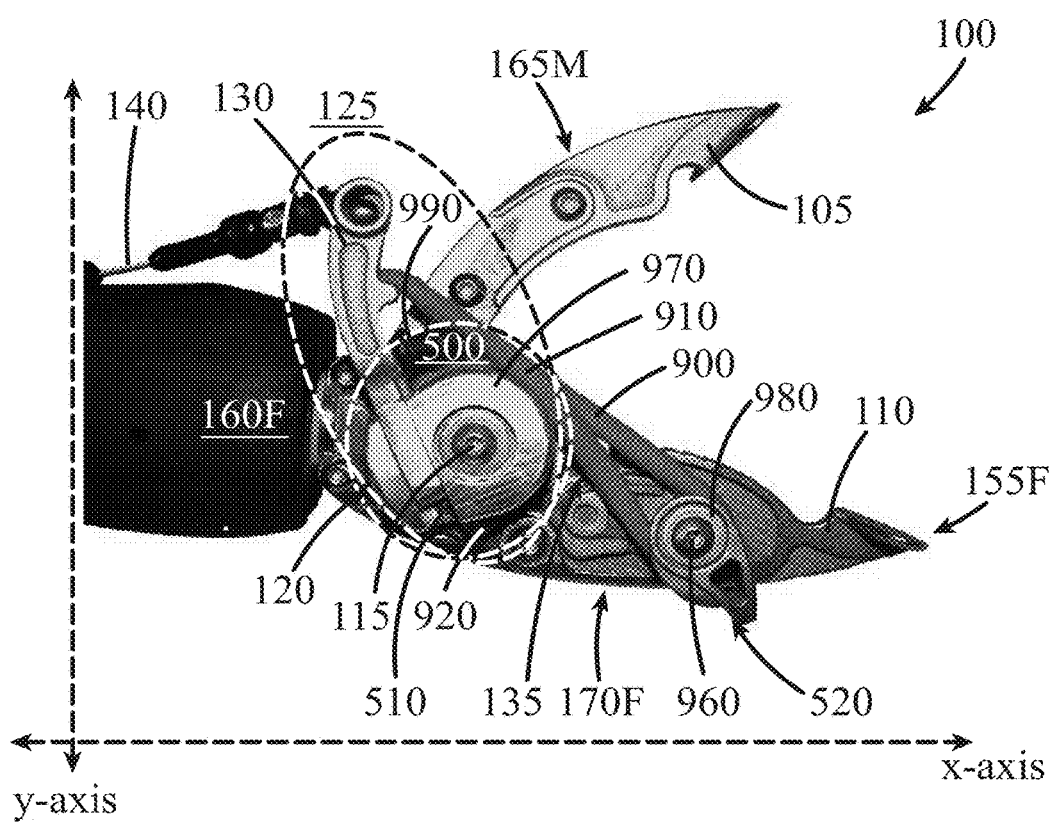
FIG. 10 illustrates a switchable prehensor in voluntary open mode, in the open position, according to some embodiments of the present disclosure.

FIGS. 9 and 10 illustrate an example of a terminal device 100 when configured to operate in VO mode. Referring again to FIG. 9, when in the VO mode and in the passively closed position (e.g. the user is not actuating the second force-generating mechanism 140, the cable), the lever 130 is in the second position, with the distal end 155L of the lever 130 positioned on the dorsal side 165F of the fixed digit 110 relative to the longitudinal x-axis and relative to the first connector 115 (e.g. pin). Referring again to FIG. 9, when the terminal device 100 is in VO mode and in the passively closed position, the distal end 155L of the lever 130 is positioned towards the distal end 155F of the fixed digit 100, relative to its longitudinal x-axis and relative to the first connector 115. The distal end 155L of the lever 130 assumes this distal position when the user is not applying an active force to the second force-generating mechanism 140 that is greater than the passive force applied to the distal end 155L of the lever 130 by the first force-generating mechanism 135, the tension cord. Thus, the passive force applied to the cable, and to the distal end 155L of the lever 130, pulls the lever 130 to its distal, closed position as shown in FIG. 9. Although the example of a first force-generating mechanism 130 shown in FIG. 9 is in the form of a length of tension cord having a first end and a second end, some embodiments of the present disclosure may include a first force-generating mechanism 130 that is in the form of continuous loop of tension cord.

FIG. 10 illustrates, for the VO mode of operation of the terminal device 100, how the various elements of the terminal device 100 interact with one another when the user applies an active force to the second force-generating mechanism 140, the cable, that is greater than the passive force provided by the first force-generating mechanism, the tension cord. When the active force provided by the user exceeds the passive force provided by the tension cord, the cable actuates/moves the distal end 155L of the lever 130 away from the distal end 155F of the fixed digit 110, towards the proximal end 155F of the fixed digit 110 (e.g. towards the user). Because the proximal end 160L of the lever 130 is fixed (although moveably/rotatably fixed) within the first channel 510 of the lever guide 500 (e.g. groove or channel), and because the lever guide 500 is secured to the fixed digit 110 at the pivot point provided by the first connector 115, actuation of the distal end 155L of the lever 130 from its distal position in front of the first connector 115 (e.g. relative to the x-axis of the longitudinal axis of the terminal device 100) to a proximal position behind the first connector 115 translates to movement of the moveable digit 100 from the passively closed position shown in FIG. 9 to the actively open position as shown in FIG. 10.

Movement of the distal end 155L of the lever 130, due to actuation of the second force-generating mechanism 140, the cable, by the user results in stretching (e.g. lengthening) of the first force-generating mechanism 135, the tension cord. Movement of the distal end 155L of the lever 130 in the proximal direction, away from the distal end 155F of the fixed digit 110 pulls the second end 930 of the first force-generating mechanism 135, which is secured within the third channel 950 of the lever 130. As the lever 130 is moved from its distal position towards its proximal position, the length of tension cord increases and intermediate portions of the tension cord, e.g. portions of the tension cord between the first end 920 and the second end 930, located at the transition from the first segment 900 to the second segment 910, move around the pulley 980 at the securement point 520. The pulley 980 minimizes friction caused by the movement of these intermediate portions of the tension cord, as these intermediate portions move around the pulley 980 due to the lengthening of the tension cord caused by the movement of the lever 130. Thus, the pulley 980 rotates around the securement point 520 as the tension cord is stretched and lengthened, and when the lever 130 is released the tension cord relaxes and shortens. Of course, the tension cord stretches and lengthens because the first end 920 of the tension cord is physically secured within the second channel 940 positioned within the second portion (e.g. substantially non-cylindrical portion) of the lever guide 500.

As mentioned above, movement of the distal end 155L of the lever 130 from a distal position to a proximal position actuates the moveable digit 100 due to the rotation of the lever guide 970 around the pivot point provided by the first connector 115. Rotation of the lever guide 970, like the movement of the lever 130, pulls on the first force-generating mechanism 135, the tension cord, and also stretches and lengthens the tension cord because of a second "lever-effect" resulting from the distance between contact point of the first segment 900 of the tension cord with the outer, circular surface of the lever guide 970, and the pivot point provided by the first connector 115. This distance is labeled "L" in FIG. 9. Thus, as a result of actuating the lever 130, the second segment 910 of the tension cord is stretched and lengthened between the distal end 155L of the lever 130 and the pulley 980, and the first segment 900 of the tension cord is stretched and lengthened between the lever guide 970 and the pulley 980. Referring to FIG. 10, as the lever 130 moves to a proximal position, a longer portion of the first segment 900 of the tension cord moves into contact with the outer circumference of the lever guide 970 (e.g. drum).

Referring again to FIG. 10, when the user releases the second force-generating mechanism 140, the cable, and the passive force provided by the first force-generating mechanism 135, the tension cord, exceeds the passive force on the cable, the passive force will pull the distal end 155L of the lever 130 from its dorsal, proximal position to its dorsal, distal position as illustrated in FIG. 9. Thus, when the passive force exceeds the active force, the tension cord will relax and shorten, pulling the distal end 155L of the lever 130 to the dorsal, distal position relative to the longitudinal x-axis of the terminal device 100. Movement of the lever 130 will in turn rotate the lever guide 970 around the pivot point provided by the first connector 115. Because the lever guide 970 is secured to the moveable digit 100, rotation of the lever guide 970 results in rotation of the moveable digit 100 around the pivot point provided by the first connector 115 until the terminal device 100 resumes the passively closed position illustrated in FIG. 9.

Figure 11:
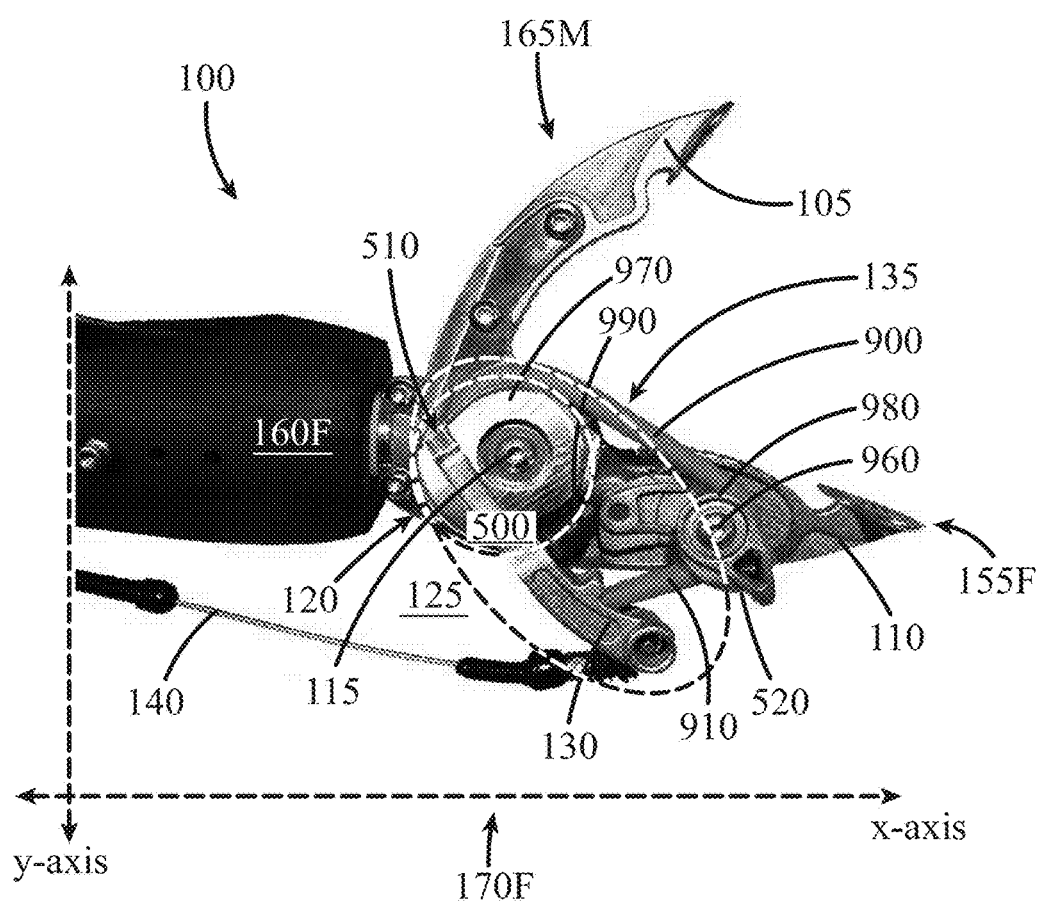
FIG. 11 illustrates a switchable prehensor in voluntary closed mode, in the open position, according to some embodiments of the present disclosure.
Figure 12:
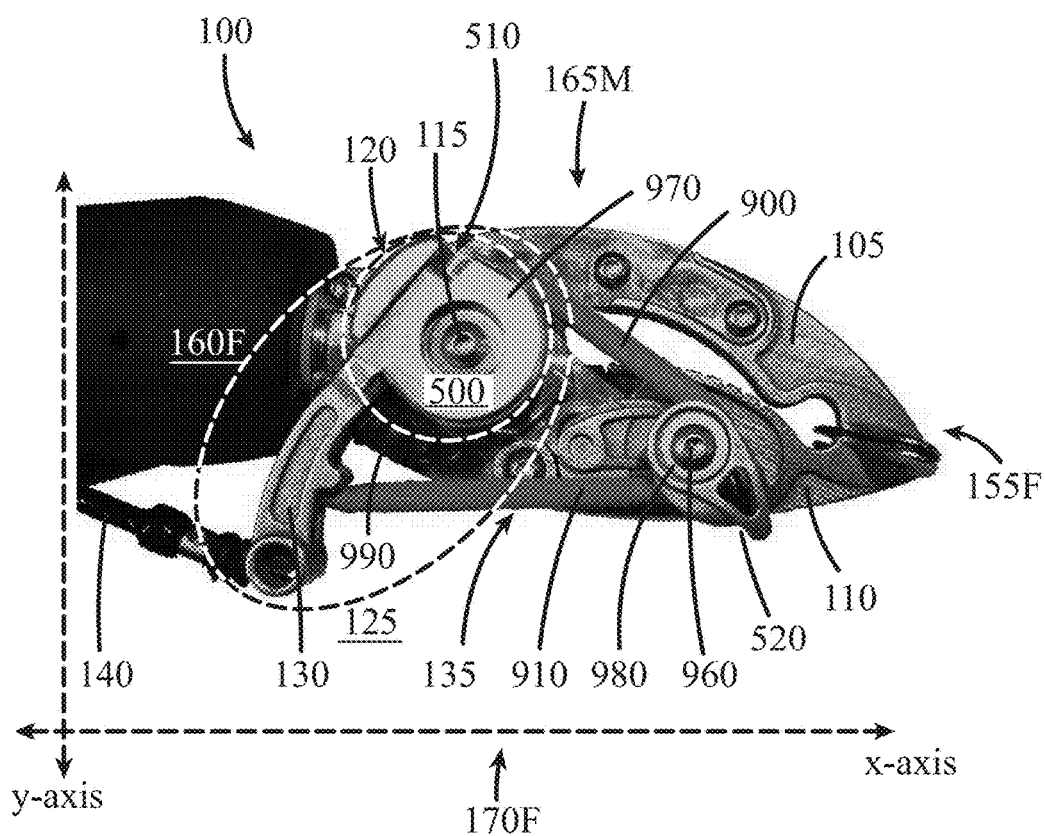
FIG. 12 illustrates a switchable prehensor in voluntary closed mode, in the closed position, according to some embodiments of the present disclosure.

FIGS. 11 and 12 illustrate the terminal device 100 configured for VC mode operation. For these examples, the distal end 155L of the lever 130 is in a palmar position relative to the longitudinal x-axis of the fixed digit 110 and the first connector 115 (e.g. a pin). Thus, a user "switches" the switchable terminal device 100 from the voluntary open mode illustrated in FIGS. 9 and 10 to the voluntary closed mode of FIGS. 11 and 12 by moving the distal end 155L of the lever 130 from the dorsal position (e.g. above the longitudinal x-axis of the terminal device 100) to the palmar position (e.g. below the longitudinal x-axis of the terminal device 100). Movement of the distal end 155L of the lever 130 is enabled due to the rotatable attachment of the proximal end 160L of the lever 130 within the lever guide 500 and to the second connector 120 (e.g. a pin). Thus, movement of the distal end 155L of the lever 130 from the dorsal position of the VO mode to the palmar position of VC mode results in the movement of the distal end 155L of the lever 130 out of a starting position located substantially in the xy-plane defined by the fixed digit 110 and the moveable digit 105, such that the distal end 155L of the lever 130 sweeps through a second plane that is at least one of perpendicular and/or non-parallel to the xy-plane. The lever 130 than moves through this second plane until the distal end 155L of the lever 130 reaches the palmar position of the VC mode, and is returned to a final position substantially within the xy-plane. The opposite movements of those just described are made by the lever 130 when switching from the VC mode to the VO mode, with the distal end 155L of the lever 130 moving from the palmar position, sweeps through the second plane, to return to the dorsal position in the xy-plane for the VO mode of operation.

Referring again to FIGS. 9 and 10, when the terminal device 100 is in VO mode, the first segment 900 and the second segment 910 of the first force-generating mechanism 135, the tension cord, cross each other and/or contact each other and/or are positioned substantially parallel to each other. Switching from the VO mode to the VC mode illustrated in FIGS. 11 and 12, by movement of the distal end 155L of the lever 130 from the dorsal position to the palmar position, removes this close relationship of the first segment 900 and the second segment 910. In addition, referring to FIG. 9, when the terminal device 100 is in the passively closed state for the VO mode, both the first segment 900 and the second segment 910 of the tension cord are stretched to a relatively longer length than the amount of stretch (and resultant length) applied to the tension cord when the terminal device 100 is in the passively open state for the VC mode, as shown in FIG. 11. Since the amount of passive force supplied by the tension cord is directly proportional to the length of tension cord, the passive force supplied by the tension cord when passively closed in the VO mode is larger than the passive force supplied by the tension cord when passively open in the VC mode. This may be desirable because a larger passive force for closing, when in VO mode, may result in a terminal device 100 that can better grasp heavier and/or awkwardly shaped items, and a smaller passive force, when in VC mode, may be desirable to avoid user fatigue when actively grasping an object for long periods of time.

As mentioned above, FIGS. 11 and 12 illustrate the switchable terminal device 100 configured for VC mode. Referring to FIG. 11, when in the VC mode and in the passively closed position (e.g. the user is not actuating the second force-generating mechanism 140, the cable), the lever 130 is in the palmar position, with the distal end 155L of the lever 130 positioned on the palmar side 170F of the fixed digit 110, relative to the longitudinal x-axis and relative to the first connector 115 (e.g. pin). In addition, when the terminal device 100 is in VC mode and in the passively open position, the distal end 155L of the lever 130 is positioned towards the distal end 155F of the fixed digit 110, relative to its longitudinal x-axis and relative to the first connector 115 (e.g. pin). The distal end 155L of the lever 130 assumes this distal position when the user is not applying an active force to the cable that is greater than the passive force applied to the distal end 155L of the lever 130 by the tension cord. Thus, the passive force applied to the cable, and to the distal end 155L of the lever 130, pulls the lever 130 to its distal, open position as shown in FIG. 11.

FIG. 12 illustrates, for the VC mode of operation, how the various elements of the terminal device 100 interact with one another when the user applies an active force to the second force-generating mechanism 140, e.g. the cable, that is greater than the passive force provided by the first force-generating mechanism 135, e.g. the tension cord. When the active force provided by the user using the cable exceeds the passive force provided by tension cord, the cable actuates/moves the distal end 155L of the lever 130 away from the distal end 155F of the fixed digit 110, towards the proximal end 160F of the fixed digit 110 (e.g. towards the user). Because the proximal end 160L of the lever 130 is fixed (although moveably/rotatably fixed) within the lever guide 500, and because the lever guide 970 is secured to the fixed digit 110 at the pivot point provided by the first connector 115 (e.g. pin), actuation of the distal end 155L of the lever 130 from its distal position in front of the first connector 115 (e.g. relative to the x-axis of the longitudinal axis of the terminal device 100) to a proximal position behind the first connector 115 translates to movement of the moveable digit 100 from the passively open position shown in FIG. 11 to the actively closed position, as shown in FIG. 12.

Referring again to FIG. 12, when the user releases the second force-generating mechanism 140, e.g. the cable, and the passive force provided by the first force-generating mechanism 135, e.g. the tension cord, exceeds the active force on the cable, the passive force will pull the distal end 155L of the lever 130 from its dorsal, proximal position to its dorsal, distal position as illustrated in FIG. 11. Thus, when the passive force exceeds the active force, the tension cord will relax and shorten, pulling the distal end 155L of the lever 130 to the dorsal, distal position relative to the longitudinal x-axis of the terminal device 100. Movement of the lever 130 will in turn rotate the lever guide 970 around the pivot point provided by the first connector 115. Because the lever guide 970 is secured to the moveable digit 100, rotation of the lever guide 970 results in rotation of the moveable digit 100 around the pivot point provided by the first connector 115 until the terminal device resumes the passively open position illustrated in FIG. 11.

Figure 13:
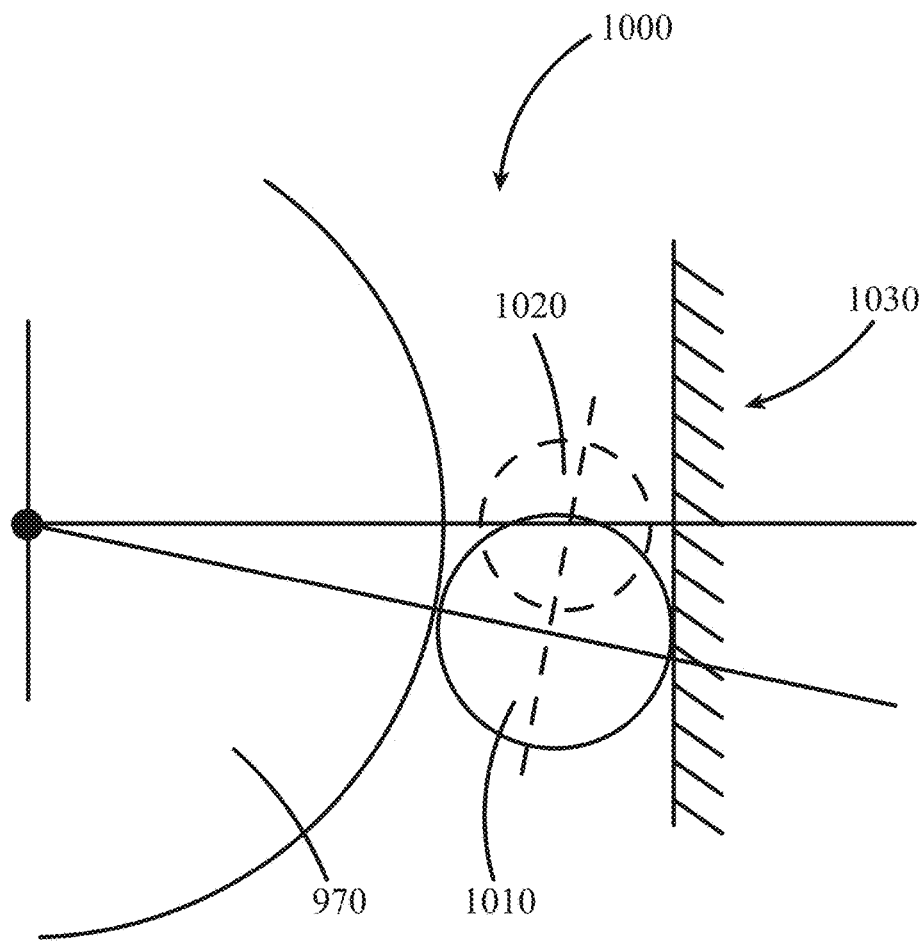
FIG. 13 illustrates a locking mechanism for a switchable prehensor when in a locked position, according to some embodiments of the present disclosure.

FIGS. 13-16 illustrates a further embodiment of the present disclosure, a locking mechanism 1000 for locking a terminal device as described above in a desired position; e.g. closed, open, and/or some position between these two extremes. Referring to FIG. 13, the locking mechanism 1000 includes a disk 1010, a magnet 1020, and a plate 1030. The positioning of the plate 1030, as described below, between the terminal device's lever guide 970 (a cylindrical drum as described above) and the plate 1030 provides a locked position and an unlocked position, where the magnet 1020 interacts with the disk 1010 to move it between the two positions. Both the disk 1010 and the magnet 1020 are magnetic, but of opposite polarity. Thus, the disk 1010 is attracted to the magnet 1020 by a magnetic force. Both, the disk 1010 and the magnet 1020 have two positions in two-dimensional space (in an xy-plane) corresponding to a locked terminal device and an unlocked terminal device. As described above, the lever guide 970 can rotate around an axis that is essentially perpendicular to the xy-plane within which the fixed digit and moveable digit operate. However, the lever guide 970 is fixed in position relative to this plane, and can only rotate clockwise and counter-clockwise. As shown in FIG. 13, the outer perimeter or edge of the lever guide 970 (e.g. drum) is separated from an outer edge of the plate 1030 by a space. The narrowest length dimension of this space is less than the diameter of the disk. However, since the lever guide 970 is cylindrical, the disk 1010 can move along a path (as indicated by the dashed line) such that the disk 1010 can be placed at a first position where the disk 1010 does not contact either the outer edge of the lever guide 970 or the outer edge of the plate 1030; this situation corresponds to the unlocked position of the locking mechanism 1000. However, movement of the disk 1010 along the path eventually places the disk 1010 in direct physical contact with both the outer edge of the lever guide 970 and the outer edge of the plate 1030 such that the disk 1010 provides sufficient friction to prevent the lever guide 970 from rotating, thus locking the lever guide 970, and therefore the moveable digit in place; this situation corresponds to the locked position of the locking mechanism 1000.

Figure 14:
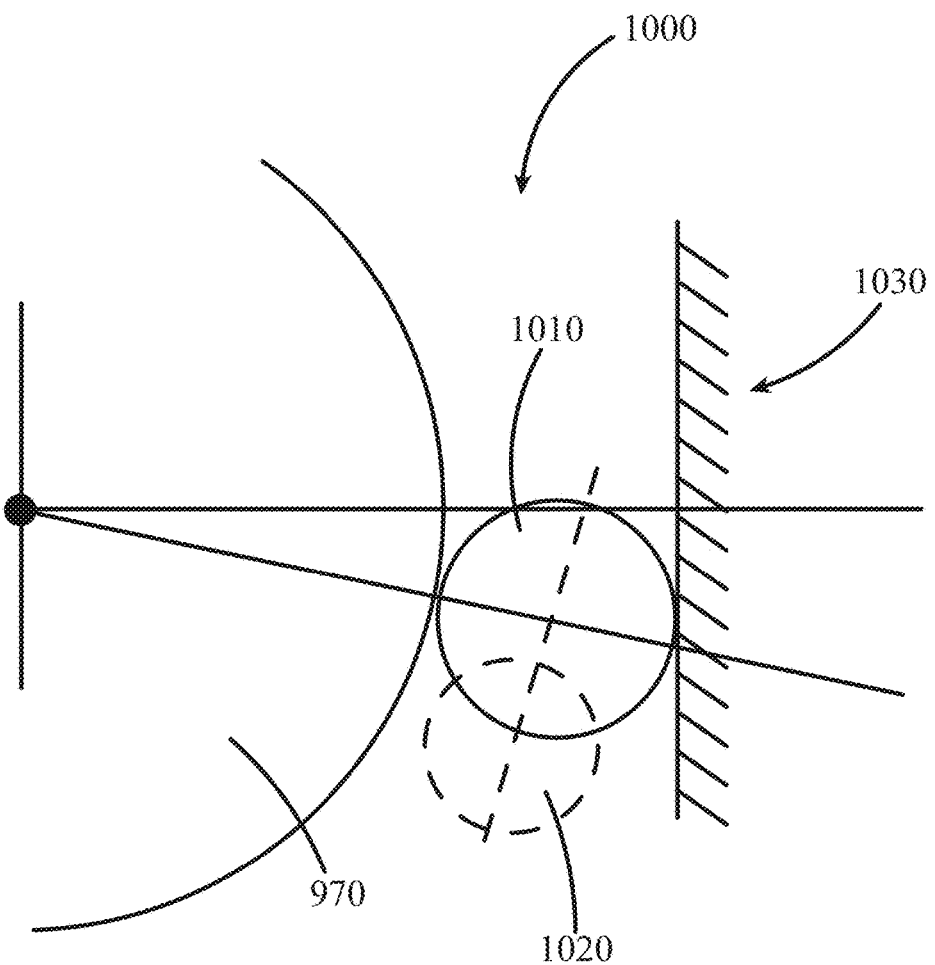
FIG. 14 illustrates a locking mechanism for a switchable prehensor when in a pre-unlocked position, according to some embodiments of the present disclosure.
Figure 15:
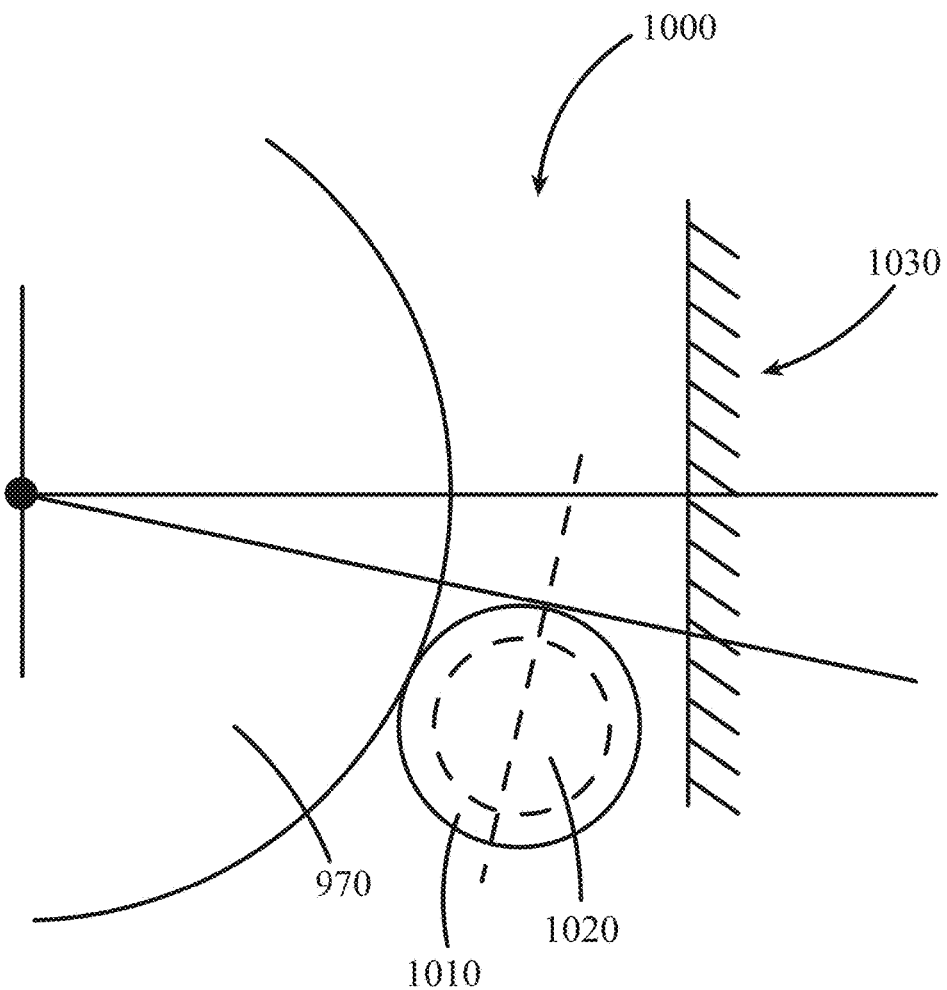
FIG. 15 illustrates a locking mechanism for a switchable prehensor when in an unlocked position, according to some embodiments of the present disclosure.

Referring again to FIG. 13, because the disk 1010 is magnetic, positioning of the magnet 1020 in a plane below the disk 1010 results in the magnet 1020 magnetically pulling the disk 1010 into contact with both the lever guide 970 and the plate 1030 and into the locking position. Thus, the magnet 1020 and the disk 1010 and in relatively close proximity to each other such that the magnetic force attracting the disk 1010 to the magnet is sufficient to hold the disk 1010 in the wedged position between the lever guide 970 and plate 1030. Counter-clockwise rotation of the lever guide 970, in particular, will maintain the disk 1010 in its wedged position between the lever guide 970 and the plate 1030. FIG. 14 illustrates a "pre-unlock state" where the user has moved the magnet 1020 into a position more towards the palmar side of the terminal device, and below the disk 1010. This second position of the magnet 1020 applies a magnetic force to the disk 1010 in a direction towards the palmar side of the terminal device. Thus, the disk 1010 has a driving force to move it out of its locked position, into the wider gap, and the unlocked position. However, the friction between the disk 1010 and the lever guide 970 and the plate 1030 are still too great to release the disk 1010 from its locked position. However, the disk 1010 may be released from the locked position by a slight clockwise rotation of the lever guide 970, as shown in FIG. 14. The clockwise rotation of the lever guide 970 reduces the friction holding the disk 1010 in contact with the lever guide 970 and the plate and, as a result, the magnet 1020 pulls the disk 1010 in the palmar direction into the wider gap, thus releasing and unlocking the lever guide 970 and allowing the lever guide 970 to freely move in either direction; clockwise and/or counter-clockwise.

Figure 16A:
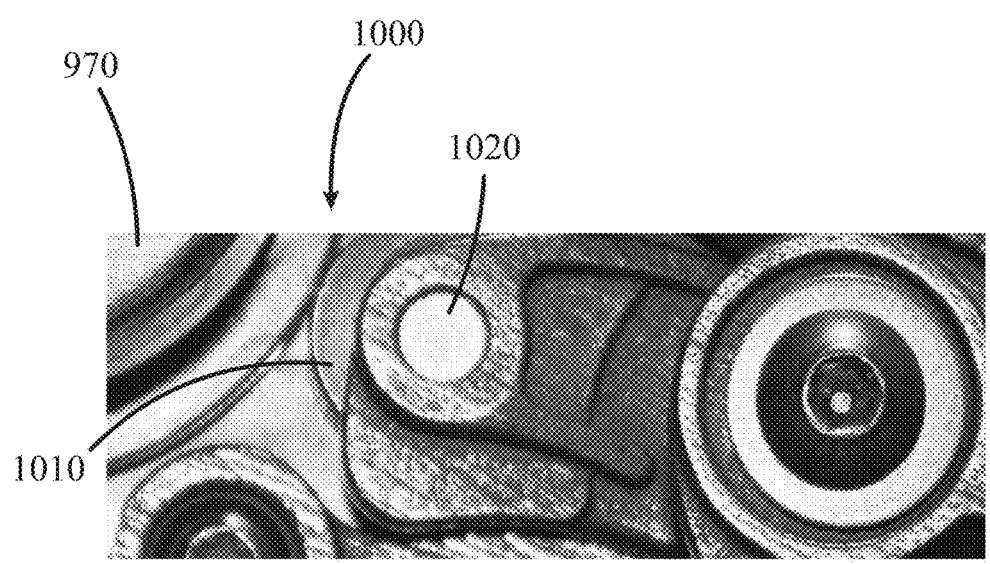
FIG. 16 illustrates a locking mechanism for a switchable prehensor when in (Panel A) a locked position and (Panel B) an unlocked position, according to some embodiments of the present disclosure.
Figure 16B:
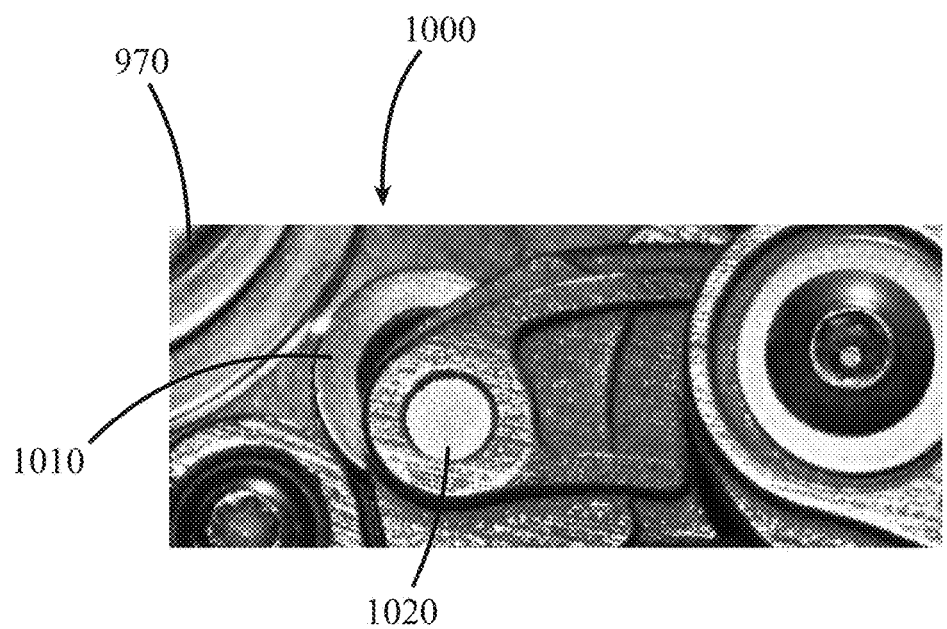

FIG. 16 illustrates an example of a locking mechanism 1000 having the features described above. Panel A of FIG. 16 illustrates the locking mechanism 1000 in its locked position with the disk 1010 in contact with an outer edge of the terminal device's lever guide 970 and the plate (not visible). The magnet is positioned in a relatively "dorsal" position to apply sufficient magnetic force to maintain the disk 1010 in its locked position. Panel B of FIG. 16 illustrates the locking mechanism 1000 in its unlocked position, where it has moved out of the narrow part of the space between the lever guide 970 and the plate (not shown) into the wider portion of the space such that the disk 1010 is not in contact with either the lever guide 970 or the plate. In this unlocked position, the magnet 1020 is shown in a more palmar location of the terminal device, which has as a result moved the disk 1010 to its unlocked position. The user may easily move the magnet 1020 by engaging the handle 1040 (e.g. with the user's other hand/thumb/finger). As shown in FIG. 16, the disk 1010 is a substantially circular piece of material, although it may be machined into any suitable geometric shape that can engage/contact the lever guide 970. The disk 1010 may have a tab (not shown) on its underside such that the tab fits into a channel and/or groove that maps the path shown in FIGS. 13-15. Thus, the disk 1010 may be locked into place, such that the disk 1010 can only move along the path defined by the channel, and where the disk 1010 is locked into this only path of movement in the xy-plane because of the placement of the disk 1010 between the moveable digit and the magnet 1020 and its associated mass. The magnet 1020 in FIG. 16 is shown as a circular piece, however, any suitably sized magnet may be used.

EXAMPLES

Example 1

A switchable terminal device comprising: a first digit having a distal end and a proximal end; a second digit moveably attached to the first digit by a first connector such that the second digit reversibly rotates around the first connector and substantially within a plane; a lever guide having a first portion and a second portion, the lever guide attached to the second digit at least by the first connector passing through the lever guide at an angle about perpendicular to the plane; a lever having a proximal end and a distal end with the proximal end of the lever moveably attached to the first portion of the lever guide by a second connector; a third connector attached near the distal end of the first digit; and an elastic cord comprising a first segment having a first end, and a second segment having a second end, wherein: the first end is attached to the first portion of the lever guide, a first part of the first segment contacts the second portion of the lever guide, a second part of the first segment spans a first distance between the lever guide and the third connector, a first part of the second segment spans a second distance between the third connector and the distal end of the lever, and the second end of the elastic cord is attached to the lever.

Example 2

The switchable terminal device of Example 1, wherein: the second portion of the lever guide is substantially cylindrical, the second portion of the lever guide comprises an outer edge, the first connector is positioned substantially centrally located in the second portion of the lever guide relative to the plane, and the first part of the first segment contacts at least a portion of the edge.

Example 3

The switchable terminal device of Example 1, wherein the outer edge comprises a groove, and the first part of the first segment is positioned within the groove.

Example 4

The switchable terminal device of Example 1, wherein the third connector comprises a rod extending from the first digit substantially perpendicular to the plane.

Example 5

The switchable terminal device of Example 4, wherein: the third connector further comprises a pulley rotatably attached to the rod, and the elastic cord is in contact with the pulley.

Example 6

The switchable terminal device of Example 1, wherein the first portion of the lever guide comprises a first channel, and the proximal end of the lever is positioned within the first channel.

Example 7

The switchable terminal device of Example 1, wherein the first portion of the lever guide comprises a second channel, and a fraction of the first segment is positioned within the second channel.

Example 8

The switchable terminal device of Example 1, wherein the distal end of the lever comprises a third channel positioned within and along at least a portion of the lever, and a fraction of the second segment is positioned within the third channel.

Example 9

The switchable terminal device of Example 1, wherein: the lever has a first position corresponding to the distal end of the lever positioned towards a palmar side of the fixed digit, the lever has a second position corresponding to the distal end of the lever positioned towards a dorsal side of the fixed digit, and the lever is capable of being reversibly switched between the first position and the second position.

Example 10

The switchable terminal device of Example 9, wherein: when in the first position, the distal end of the lever is positioned towards the distal end of the fixed digit or towards the proximal end of the fixed digit, when in the second position, the distal end of the lever is positioned towards the distal end of the fixed digit or towards the proximal end of the fixed digit, when the distal end of the lever is in the first position and positioned towards the distal end of the fixed digit, the tension cord provides a first force, and when the distal end of the lever is in the second position and positioned towards the distal end of the fixed digit, the tension cord provides a second force that is greater than the first force.

Example 11

The switchable terminal device of Example 9, wherein the first force is between about 2 $lb_f$ and about 5 $lb_f$.

Example 12

The switchable terminal device of Example 9, wherein: when the distal end of the lever is in the second position, the first segment and the second segment form at least one of a crossing point or a contact point, and when the distal end of the lever is in the first position, the first segment and the second segment do not form the crossing point or the contact point.

Example 13

The switchable terminal device of Example 1, wherein the first connector comprises at least one of a pin, a screw, a rivet, a nail, a shaft, or a rod.

Example 14

The switchable terminal device of Example 1, wherein the second connector comprises at least one of a pin, a screw, a rivet, a nail, a shaft, or a rod.

Example 15

The switchable terminal device of Example 1, further comprising a locking mechanism positioned at the third connector, wherein: the locking mechanism has a locked position and an unlocked position, the locked position prevents the second digit from rotating around the first connector, and the unlocked position allows the second digit to rotate around the first connector.

Example 16

A method for actuating a switchable terminal device, the method comprising: attaching, using a connector, a first digit having a distal end and a proximal end to a second digit, wherein the second digit is rotatable relative to the first digit, around the first connector, and substantially within a first plane; affixing a lever guide having a first portion and a second portion to the second digit such that the first connector passes through a point substantially near the center of the lever guide at an angle about perpendicular to the first plane; securing a lever having a proximal end and a distal end by moveably attaching the proximal end of the lever to the first portion of the lever guide using a second connector; positioning a third connector near the distal end of the first digit; attaching to the lever guide an elastic cord comprising a first segment having a first end, and a second segment having a second end, such that the first end is attached to the first portion of the lever guide; passing at least a part of the first segment over the second portion of the lever guide; traversing with the first segment a first distance between the lever guide and the third connector; contacting the third connector with a portion of the elastic cord; traversing with the second segment a second distance between the lever guide and the distal end of the lever; and connecting the second end to the distal end of the lever.

Example 17

The method of Example 16, further comprising reversibly switching the lever from a first position corresponding to the distal end of the lever positioned towards a palmar side of the fixed digit to a second position corresponding to the distal end of the lever positioned towards a dorsal side of the fixed digit, wherein the switching is performed by moving the distal end of the lever through a second plane that is not parallel to the first plane.

Example 18

The method of Example 17, further comprising: when in the first position, actuating the distal end of the lever by moving the distal end of the lever from a first distal location to a first proximal location results in the terminal device transitioning from open to closed, and when in the second position, actuating the distal end of the lever by moving the distal end of the lever from a second distal location to a second proximal location results in the terminal device transitioning from closed to open.

Example 19

The method of Example 18, wherein, when in the first position and the first distal location, applying a first force to the distal end of the lever, that is less than a second force applied to the distal end of the lever when in the second position and the second distal location.

Example 20

The method of Example 17, further comprising: crossing the first segment relative to the second segment when switching the lever from the first position to the second position; and uncrossing the first segment relative to the second segment when switching the lever from the second position to the first position.

Example 21

A locking mechanism comprising: a lever guide (e.g. drum) separated from a plate by a space having a narrow section and a wide section; and a disk moveable between a first position and a second position along a first path within a first plane, wherein: when the disk is in the first position, the disk is positioned on the first path in the narrow section such that the disk is in physical contact with the lever guide and the plate such that the lever guide may not rotate, and when the disk is in the second position, the disk is positioned on the first path in the wide section such that the disk does not contact the lever guide or the plate such that the lever guide is free to rotate.

Example 22

The locking mechanism of Example 20, further comprising: a magnet moveable between a third position and a fourth position along a second path with a second plane that is parallel to the first plane, and along a second path that substantially mirrors the first path, wherein: the disk is sufficiently magnetic to be attracted by the magnet such that placement of the magnet in the third position will provide a first magnetic force that biases the disk to the first position, and placement of the magnet in the fourth position will provide a second magnetic force that biases the disk to the second position.

Example 23

The locking mechanism of Example 21, wherein the magnet is positioned in a body configured to be actuated by a user to reversibly move the magnet between the third position and the fourth position.

The foregoing discussion and examples have been presented for purposes of illustration and description. The foregoing is not intended to limit the aspects, embodiments, or configurations to the form or forms disclosed herein. In the foregoing Detailed Description for example, various features of the aspects, embodiments, or configurations are grouped together in one or more embodiments, configurations, or aspects for the purpose of streamlining the disclosure. The features of the aspects, embodiments, or configurations, may be combined in alternate aspects, embodiments, or configurations other than those discussed above. This method of disclosure is not to be interpreted as reflecting an intention that the aspects, embodiments, or configurations require more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate aspect, embodiment, or configuration.

What is claimed is:
1. A switchable terminal device comprising:
a first digit having a distal end and a proximal end;
a second digit moveably attached to the first digit by a first connector such that the second digit reversibly rotates around the first connector and substantially within a plane;

a lever guide having a first portion and a second portion, the lever guide attached to the second digit by the first connector passing through the lever guide at an angle about perpendicular to the plane;

a lever having a proximal end and a distal end with the proximal end of the lever moveably attached to the first portion of the lever guide by a second connector;

a third connector attached near the distal end of the first digit; and an elastic cord comprising a first segment having a first end, and a second segment having a second end, wherein:

the first end is attached to the first portion of the lever guide, a first part of the first segment contacts the second portion of the lever guide, a second part of the first segment spans a first distance between the lever guide and the third connector, a first part of the second segment spans a second distance between the third connector and the distal end of the lever, and the second end of the elastic cord is attached to the lever.

2. The switchable terminal device of claim 1, wherein:
the second portion of the lever guide is substantially cylindrical,
the second portion of the lever guide comprises an outer edge,
the first connector is positioned substantially centrally located in the second portion of the lever guide relative to the plane, and
the first part of the first segment contacts at least a portion of the edge.

3. The switchable terminal device of claim 1, wherein the outer edge comprises a groove, and the first part of the first segment is positioned within the groove.

4. The switchable terminal device of claim 1, wherein the third connector comprises a rod extending from the first digit substantially perpendicular to the plane.

5. The switchable terminal device of claim 4, wherein:
the third connector further comprises a pulley rotatably attached to the rod, and
the elastic cord is in contact with the pulley.

6. The switchable terminal device of claim 1, wherein the first portion of the lever guide comprises a first channel, and the proximal end of the lever is positioned within the first channel.

7. The switchable terminal device of claim 1, wherein the first portion of the lever guide comprises a second channel, and a fraction of the first segment is positioned within the second channel.

8. The switchable terminal device of claim 1, wherein the distal end of the lever comprises a third channel positioned within and along at least a portion of the lever, and a fraction of the second segment is positioned within the third channel.

9. The switchable terminal device of claim 1, wherein:
the lever has a first position corresponding to the distal end of the lever positioned towards a palmar side of the fixed digit,
the lever has a second position corresponding to the distal end of the lever positioned towards a dorsal side of the fixed digit, and
the lever is capable of being reversibly switched between the first position and the second position.

10. The switchable terminal device of claim 9, wherein:
when in the first position, the distal end of the lever is positioned towards the distal end of the fixed digit or towards the proximal end of the fixed digit,
when in the second position, the distal end of the lever is positioned towards the distal end of the fixed digit or towards the proximal end of the fixed digit,
when the distal end of the lever is in the first position and positioned towards the distal end of the fixed digit, the tension cord provides a first force, and
when the distal end of the lever is in the second position and positioned towards the distal end of the fixed digit, the tension cord provides a second force that is greater than the first force.

11. The switchable terminal device of claim 9, wherein the first force is between about 2 $lb_f$ and about 5 $lb_f$.

12. The switchable terminal device of claim 9, wherein:
when the distal end of the lever is in the second position, the first segment and the second segment form at least one of a crossing point or a contact point, and
when the distal end of the lever is in the first position, the first segment and the second segment do not form the crossing point or the contact point.

13. The switchable terminal device of claim 1, wherein the first connector comprises at least one of a pin, a screw, a rivet, a nail, a shaft, or a rod.

14. The switchable terminal device of claim 1, further comprising a locking mechanism positioned at the third connector, wherein:
the locking mechanism has a locked position and an unlocked position,
the locked position prevents the second digit from rotating around the first connector, and
the unlocked position allows the second digit to rotate around the first connector.

15. A method for actuating a switchable terminal device, the method comprising:
attaching, using a connector, a first digit having a distal end and a proximal end to a second digit, wherein the second digit is rotatable relative to the first digit, around the first connector, and substantially within a first plane;
affixing a lever guide having a first portion and a second portion to the second digit such that the first connector passes through a point substantially near the center of the lever guide at an angle about perpendicular to the first plane;
securing a lever having a proximal end and a distal end by moveably attaching the proximal end of the lever to the first portion of the lever guide using a second connector;
positioning a third connector near the distal end of the first digit;
attaching to the lever guide an elastic cord comprising a first segment having a first end, and a second segment having a second end, such that the first end is attached to the first portion of the lever guide;
passing at least a part of the first segment over the second portion of the lever guide;
traversing with the first segment a first distance between the lever guide and the third connector;
contacting the third connector with a portion of the elastic cord;
traversing with the second segment a second distance between the lever guide and the distal end of the lever; and
connecting the second end to the distal end of the lever.

16. The method of claim 15, further comprising reversibly switching the lever from a first position corresponding to the distal end of the lever positioned towards a palmar side of the fixed digit to a second position corresponding to the distal end of the lever positioned towards a dorsal side of the fixed digit, wherein the switching is performed by moving the distal end of the lever through a second plane that is not parallel to the first plane.

17. The method of claim 16, further comprising:
when in the first position, actuating the distal end of the lever by moving the distal end of the lever from a first distal location to a first proximal location results in the terminal device transitioning from open to closed, and
when in the second position, actuating the distal end of the lever by moving the distal end of the lever from a second distal location to a second proximal location results in the terminal device transitioning from closed to open.

18. The method of claim 17, wherein, when in the first position and the first distal location, applying a first force to the distal end of the lever, that is less than a second force applied to the distal end of the lever when in the second position and the second distal location.

19. The method of claim 18, further comprising:
crossing the first segment relative to the second segment when switching the lever from the first position to the second position; and
uncrossing the first segment relative to the second segment when switching the lever from the second position to the first position.

* * * * *